US009733222B2

(12) United States Patent
Hudalla et al.

(10) Patent No.: US 9,733,222 B2
(45) Date of Patent: Aug. 15, 2017

(54) RAPID ANALYSIS OF STEROIDS AND STEROID DERIVATIVES

(71) Applicant: Waters Technologies Corporation, Milford, MA (US)

(72) Inventors: Christopher J. Hudalla, Milford, MA (US); Jacob N. Fairchild, Upton, MA (US); Jason F. Hill, Milford, MA (US)

(73) Assignee: Waters Technologies Corporation, Milford, MA (US)

( * ) Notice: Subject to any disclaimer, the term of this patent is extended or adjusted under 35 U.S.C. 154(b) by 65 days.

(21) Appl. No.: 14/432,313

(22) PCT Filed: Oct. 2, 2013

(86) PCT No.: PCT/US2013/063051
§ 371 (c)(1),
(2) Date: Mar. 30, 2015

(87) PCT Pub. No.: WO2014/055638
PCT Pub. Date: Apr. 10, 2014

(65) Prior Publication Data
US 2015/0276690 A1 Oct. 1, 2015

Related U.S. Application Data

(60) Provisional application No. 61/744,892, filed on Oct. 3, 2012.

(51) Int. Cl.
*B01J 20/281* (2006.01)
*B01J 20/02* (2006.01)
(Continued)

(52) U.S. Cl.
CPC ......... *G01N 30/482* (2013.01); *B01D 15/322* (2013.01); *B01D 15/42* (2013.01);
(Continued)

(58) Field of Classification Search
None
See application file for complete search history.

(56) References Cited

U.S. PATENT DOCUMENTS

| | | | |
|---|---|---|---|
| 2002/0102563 A1* | 8/2002 | Gjerde | C12N 15/101 435/6.16 |
| 2008/0093300 A1* | 4/2008 | Clarke | B01J 20/28083 210/656 |
| 2009/0092776 A1 | 4/2009 | Betz et al. | |
| 2010/0307226 A1 | 12/2010 | Cooper et al. | |

(Continued)

FOREIGN PATENT DOCUMENTS

EP 1097985 B1 5/2001

OTHER PUBLICATIONS

Coville, Neil J., et al., "Mesoporous Ethanesilica Materials with Bimodal and Trimodal Pore-Size Distributions Synthesized in the Presence of Cobalt Ions," South African Journal of Science, vol. 106, No. 7/8, Article #213, Jul. 26, 2010, parges 1-5.
Waters Corporation, "A Review of Waters Hybrid Particle Technology. Part 2. Ethylene-Bridged [BEH Technology] Hybrids and Their Use in Liquid Chromatography," 2005, pp. 1-8.
(Continued)

*Primary Examiner* — Robert R Raevis
(74) *Attorney, Agent, or Firm* — McCarter & English, LLP; Deborah M. Vernon; Michael J. DeGrazia

(57) ABSTRACT

The subject technology is directed to a $CO_2$-based chromatography system and method for rapid determination of the levels and/or the presence or absence of steroids or steroid derivatives in a sample.

26 Claims, 20 Drawing Sheets

(51) Int. Cl.

| | | |
|---|---|---|
| *B01J 20/28* | (2006.01) | |
| *B01J 20/286* | (2006.01) | |
| *B01J 20/32* | (2006.01) | |
| *B01J 20/10* | (2006.01) | |
| *B01D 15/32* | (2006.01) | |
| *B01D 15/42* | (2006.01) | |
| *G01N 30/06* | (2006.01) | |
| *G01N 30/22* | (2006.01) | |
| *B01J 20/06* | (2006.01) | |
| *B01J 20/20* | (2006.01) | |
| *G01N 30/88* | (2006.01) | |
| *G01N 30/00* | (2006.01) | |

(52) U.S. Cl.
CPC ............. *B01J 20/02* (2013.01); *B01J 20/06* (2013.01); *B01J 20/103* (2013.01); *B01J 20/20* (2013.01); *B01J 20/205* (2013.01); *B01J 20/286* (2013.01); *B01J 20/28069* (2013.01); *B01J 20/28078* (2013.01); *B01J 20/3251* (2013.01); *B01J 20/3293* (2013.01); *G01N 30/06* (2013.01); *G01N 30/22* (2013.01); *B01J 2220/58* (2013.01); *G01N 2030/484* (2013.01); *G01N 2030/8813* (2013.01); *G01N 2333/575* (2013.01)

(56) References Cited

U.S. PATENT DOCUMENTS

2013/0203589 A1* 8/2013 Thompson ............. B01J 20/283
  502/413
2014/0220116 A1* 8/2014 Brahmbhatt ......... A61K 9/5068
  424/450

OTHER PUBLICATIONS

International Search Report, International Application no. PCT/US13/63051; International Filing Date: Oct. 2, 2013, 17 pages, Mailing Date: Feb. 2, 2014.

Kamangerpour, A., et al., "Supercritical Fluid Chromatography of Polyphenolic Compounds in Grape Seed Extract," Chromatographia, vol. 55, No. 7/8, Apr. 2002, pp. 417-481.

Nomura, A., et al., "Determination of Free Fatty Acids by Supercritical Fluid Chromatography on an ODS Silica-Gel Column," Analytical Sciences, vol. 11, Jun. 1995, pp. 385-388.

Kobata, K., et al., "Supercritical $CO_2$ as a Reaction Medium for Synthesis of Capsaicin Analogues by Lipase-Catalyzed Transacylation of Capsaicin," Biotechnology Letters, vol. 25, No. 18, Sep. 2003, pp. 1575-1578.

Dong, M.W., "Modern HPLC for Practicing Scientists," John Wiley & Sons, 2006, 6 pages.

Vickery, T.M., "Liquid Chromatography Detectors," Chromatographic Science Series, vol. 23, New York: Marcel Dekker, Inc., 1983.

* cited by examiner

RAPID ANALYSIS OF STEROIDS AND STEROID DERIVATIVES

RELATED APPLICATIONS

This application is a 35 U.S.C. §371 national stage filing of International Application No. PCT/US2013/063051, filed Oct. 2, 2013, which claims the priority benefit of U.S. Provisional Application No. 61/744,892, filed Oct. 3, 2012, the entire content of each of which is incorporated herein by reference in its entirety as though fully set forth herein.

FIELD

The subject technology relates to $CO_2$-based chromatography; in particular, the subject technology relates to a $CO_2$-based chromatography system ("$CO_2$-based system") and method for rapid qualitative and/or quantitative analysis of steroids and steroid derivatives.

BACKGROUND

Steroid regulation plays a central role in the health and development of adults and children. Disrupted or altered regulation of steroids is associated with a wide host of diseases, including Addison Disease, congenital hyperplasia, Cushing's disease, Hirsutism, Conn's disease, polycystic ovary disease and gynecomastia, among others. Often disease states will differ based on subtle variations in the amount of or the complex series of interactions among the many different steroids. Differential diagnosis, therefore, depends on the simultaneous and quantitative analysis of multiple steroids.

Steroid biosynthesis is a complex metabolic pathway utilizing simple precursors to synthesize multiple steroidal forms. This biosynthetic pathway that is unique to animals provides a common target for antibiotics and other anti-infective drugs. In addition, synthetic steroids and steroid derivatives are frequently used in therapeutic applications. Many of the steroid structures are closely related making their analysis challenging even when using the selectivity of mass spectrometric detection. Chromatographic separation is therefore essential for accurate and precise analysis of clinically relevant steroids and steroid derivatives.

Typical methods for analysis of steroids and steroid derivatives include Immunoassay (IA), GC/MS, and LC/MS/MS. However, there are shortcomings associated with each of these methods. For example, the IA methods are non-specific, time-consuming, labor-intensive and do not lend themselves well to rapid or high throughput analyses of multiple analytes or samples. The gas chromatography/mass spectroscopy (GC/MS) methods require sample samples. The gas chromatography/mass spectroscopy (GC/MS) methods require sample derivitization prior to GC analysis, which is burdensome and time-consuming. In LC/MS/MS methods, although no sample derivitization is required, the typical run time of a sample on an HPLC (high performance or pressure liquid chromatography) instrument is about 12 minutes; which has recently been reduced to about 4-5 minutes by using a UHPLC (ultra high performance or pressure chromatography) instrument. However, there are several disadvantages to using HPLC or UHPLC, one of which being their using of toxic organic solvents as mobile phase and generating excess toxic waste, which is expensive to purchase and dispose of.

The use of non-toxic Supercritical $CO_2$ (SC—$CO_2$) as an alternative to organic solvents as the mobile phase has resulted in the advent of supercritical fluid chromatography (SFC) which embraces many of the features of liquid and gas chromatography. Theoretically, SC—$CO_2$ provides a low viscosity mobile phase that achieves higher diffusion rates and enhanced mass transfer over the solvents used in HPLC. However, the current SFC instruments (which are mainly retooled HPLCs) and methods have many limitations including, for example, long sample run time, inaccurate or imprecise control over the mobile phase density and composition, inability to reliably modifiers at low amounts (<5% per volume of $CO_2$), susceptibility to system pressure fluctuations and sample backflow, baseline noise, sample carryover, and lack of robustness, which prevent users from rapidly obtaining reproducible results.

Therefore, there still remains a need for an improved chromatography system and method that overcomes one or more of the above limitations and allow for a rapid and robust analysis of steroids and steroid derivatives.

SUMMARY

The subject technology is illustrated, for example, according to various aspects described below.

In one aspect, the subject technology is based, in part, on the discovery that the $CO_2$-based system and method disclosed herein—featuring a chromatography column, packed with a solid stationary phase of inorganic or inorganic/organic hybrid particles having a polar or polar/non-polar surface functionality, with a mean particle size of about 1.7 microns—reproducibly resolved a mixture of steroids and steroid derivatives in approximately two minutes.

In another aspect, the subject technology is based, in part, on the discovery that the $CO_2$ based system and method disclosed herein allows for rapid and reproducible separation and analysis of steroids or steroid derivatives which are similar in structure or identical in molecular weight.

In another aspect, the subject technology relates to a chromatography method for detecting one or more steroids or steroid derivatives in a sample including the steps of:

providing a sample containing one or more steroids or steroid derivatives for analysis; wherein the sample is prepared with, extracted or dissolved in a diluent comprising at least about 60% organic solvent, with the proviso that the sample is not subject to a solvent exchange step once it is prepared or before analysis by the method of the subject technology;

applying the sample to a chromatography column with a solid stationary phase including inorganic or hybrid particles having a mean particle size of about 0.5 to about 3.5 microns; wherein said particles have a polar or polar/non-polar surface functionality and retain said one or more steroids or steroid derivatives;

eluting the one or more steroids or steroid derivatives from the chromatography column by a mobile phase including a mixture of CO2 and a modifier to form one or more eluted steroids or steroid derivatives, and detecting said one or more eluted steroids or steroid derivatives by a suitable detecting device.

In an embodiment related to this or any other aspects of the subject technology, the sample includes a biological sample or a non-biological sample or a mixture thereof. In another related embodiment, the particles have a mean particle size of about 0.5 to about 2 microns. In another related embodiment, the particles have a mean pore volume in the range of about 0.1 to about 2.5 cm/g. In another related embodiment, the particles have a mean pore diameter in the range of about 100 to about 1000 Angstroms. In another related embodiment, the inorganic particles include silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof. In another related embodiment, the hybrid particles include an inorganic portion and an organic portion. In another related embodiment, the inorganic portion of the hybrid particles include comprise silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof. In another related embodiment, the organic portion of the hybrid particles include substituted or unsubstituted C1-C18 alkane, alkylene, alkenylene, alkynylene or arylene moiety bonded to one or more atoms of the inorganic portion. In another related embodiment, the organic portion of the hybrid particles include substituted or unsubstituted C1-C18 alkylene, alkenylene, alkynylene or arylene moiety bridging two or more atoms of the inorganic portion. In another related embodiment, the particles include free surface hydroxyl groups, free surface silanol groups or surface modifications with embedded polar functional groups. In another related embodiment, the particles include free surface hydroxyl groups or free surface silanol groups and surface modifications with non-polar functional groups. In another related embodiment, the chromatography column is kept in temperature range of about 5° C. to about 85° C. In another related embodiment, the modifier is mixed with the CO2 under a constant or gradient condition or both over an elution period or a fraction thereof. In another related embodiment, the modifier is a polar water-miscible organic solvent including at least one of methanol, ethanol, isopropanol, acetonitrile, acetone, tetrahydrofuran or water. In another related embodiment, the gradient condition includes increasing or decreasing flow volume of the modifier over the elution period or a fraction thereof. In another related embodiment, the elution period is about 2 min. In another related embodiment, the gradient condition includes increasing the flow volume of the modifier from about 0% to about 40% (v/v CO2) or any intervals therebetween. In another related embodiment, the gradient condition includes increasing the flow volume of the modifier from about 1% to about 17% (v/v CO2). In another related embodiment, the CO2 is liquid CO2 in subcritical or supercritical state or both. In another related embodiment, the detection comprises determining the level or the presence or absence of the one or more steroids or steroid derivatives. In another related embodiment, the detection is by way of a UV detector; a mass spectrometer; Evaporative Light Scattering (ELS) detector or a photodiode array detector (PDA). In another related embodiment, the sample is not subject to a derivatization step because the method of the subject technology is sufficiently sensitive to detect minute amounts of steroids or steroid derivatives in the sample. In another related embodiment, the chromatography column has a length of about 50 to 150 mm and an internal diameter about 2 to 4 mm. In another related embodiment, the chromatography column is part of a chromatography system including a pre-column mobile phase dwell volume of about 100 to 500 µL; wherein said pre-column mobile phase dwell volume is the volume of the mobile phase present in a fluidic connection between a junction at which the $CO_2$ and the modifier are mixed and the head of the chromatography column. In another related embodiment, the one or more steroids or steroid derivatives are eluted from the chromatography column by the mobile phase with a flow rate of about 1 to 4 mL/min. In another related embodiment, In another aspect, the subject technology relates to a chromatography method for detecting one or more steroids or steroid derivatives including:

(1) providing a sample including one or more steroids or steroid derivatives for analysis; wherein the sample is prepared with, extracted or dissolved in a diluent comprising at least 60% organic solvent, with the proviso that the sample is not subject to a solvent exchange step;

(2) applying the sample to a chromatography apparatus including:

(a) a column with a solid stationary phase including an inorganic or hybrid particle having a mean particle size of about 0.5 to about 3.5 microns, wherein said particle has a polar or polar/non-polar surface functionality, wherein said column has a length of about 50 to 150 mm and an internal diameter about 2 to 4 mm, and wherein the solid stationary phase retains said one or more steroids or steroid derivatives;

(b) a pre-column mobile phase dwell volume of about 75 µL to about 500 µL; wherein said pre-column dwell volume comprises a space within a tubular connection between a junction at which two or more mobile phase solvents (e.g., liquid $CO_2$ and a modifier) are mixed to the head of the column;

(c) a post-column mobile phase dwell volume of about 10 µL to about 450 µL; wherein said post-column dwell volume occupies a space within a tubular connection between the end of the column and a detector;

(3) eluting the one or more steroids or steroid derivatives from the chromatography column by a mobile phase including a mixture of $CO_2$ and a modifier to form one or more eluted steroids or steroid derivatives, wherein the mobile phase has a flow rate of about 1 to 4 mL/min; and (4) detecting said one or more eluted steroids or steroid derivatives with a suitable detector.

In another aspect, the subject technology relates to a kit for performing analysis or detecting one or more steroids or steroid derivatives in a sample, including:

a sample preparation device for preparing the sample including one or more steroids or steroid derivatives for analysis; wherein the sample is prepared with, extracted or dissolved in a diluent comprising at least about 60% organic solvent, with the proviso that the sample is analyzed without a solvent exchange step;

a chromatography column with a solid stationary phase including inorganic or hybrid particles having a mean particle size of 0.5 to 3.5 microns; wherein said particles have a polar or polar/non-polar surface functionality and retain said one or more steroids or steroid derivatives;

one or more standards for calibrating and facilitating the analysis and detection of the one or more eluted steroids or steroid derivatives.

In another aspect, the subject technology relates to a system for detecting one or more steroids or steroid derivatives, said system including (a) a column with a solid stationary phase including an inorganic or hybrid particle having a mean particle size of about 0.5 to about 3.5 microns, wherein said column has a length of about 50 to 150 mm and an internal diameter about 2 to 4 mm, and wherein the solid stationary phase retains said one or more steroids or steroid derivatives; (b) a pre-column mobile phase dwell volume of about 75 µL to about 500 µL; wherein said pre-column dwell volume comprises a space within a tubular connection between a junction at which two or more mobile phase solvents are mixed to the head of the column; (c) a post-column mobile phase dwell volume of about 10 μL to about 450 μL; wherein said post-column dwell volume occupies a space within a tubular connection between the end of the column and a detector.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology. Like reference numbers indicate like elements.

DETAILED DESCRIPTION

Figure 1:
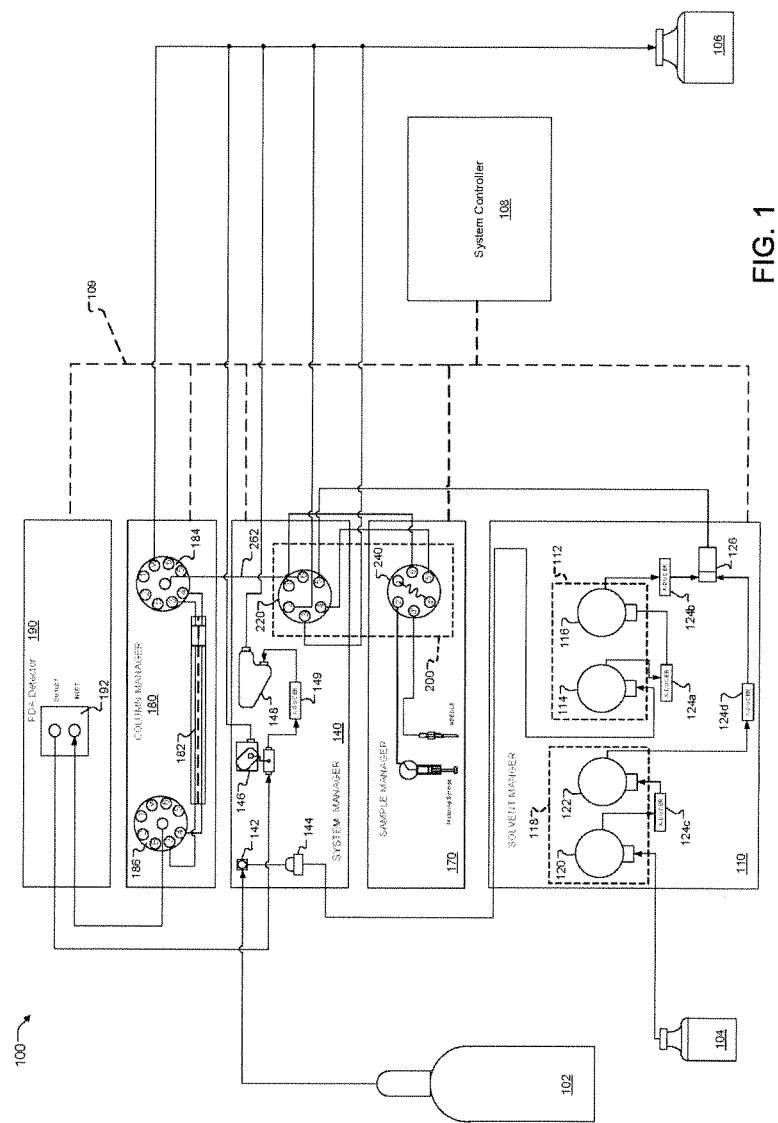
FIG. 1 is a schematic view of an exemplary $CO_2$-based system of the subject technology.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Definitions

To facilitate an understanding of the present subject technology, a number of terms and phrases are defined below:

A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Underlined, bold and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

As used herein, the term "steroids" refers to any natural or synthetic steroids and derivatives thereof, with a chemical structure that contains the core of gonane or a skeleton derived therefrom. Gonane is the simplest possible steroid and is composed of seventeen carbon atoms, bonded together to form four fused rings. The three cyclohexane rings (designated as rings A, B, and C) form the skeleton of phenanthrene; ring D has a cyclopentane structure. Generally, the steroids vary by the functional groups attached to this four-ring core and by the oxidation state of the rings. The term steroids further include sterols which are special forms of steroids, with a hydroxyl group at position-3 and a skeleton derived from cholestane. Examples of steroids include, but are not limited to, the dietary fat cholesterol, the sex hormones estradiol and testosterone, and the anti-inflammatory drug dexamethasone, or others listed or depicted herein.

As used herein, the term "hybrid", as in hybrid particles or organic-inorganic hybrid material, includes inorganic-based structures wherein an organic functionality is integral to both the internal or "skeletal" inorganic structure as well as the hybrid particle surface. The inorganic portion of the hybrid particle can be, e.g., silicone, aluminum, titanium, cerium, zirconium, barium, cobalt, copper, europium, gadolinium, iron, nickel, samarium, silver, titanium, diamond, zinc, boron or oxides thereof, or silicon carbide, carbon black, carbon nanotubes, ceramic, glass, metallic materials or mixtures thereof. The organic functionality includes organic functional groups which impart a certain chromatographic functionality to a stationary phase. Exemplary organic functional groups are substituted or unsubstituted aliphatic groups, alicyclic groups, heterocyclic groups, aromatic groups, amino groups and the like. Exemplary hybrid materials or particles are further described in U.S. Pat. Nos. 4,017,528, 6,528,167, 6,686,035 and 7,175,913, each of which is hereby incorporated herein by reference.

The term "aliphatic group" includes organic compounds characterized by straight or branched chains, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl, and the like. As used herein, the term "nitro" means —$NO_2$; the term "halogen" designates —F, —Cl, —Br or —I; the term "thiol" means SH; and the term "hydroxyl" means —OH. The term "alkylamino" as used herein means an alkyl group, as defined above, having an amino group attached thereto. Suitable alkylamino groups include groups having 1 to about 12 carbon atoms, or from 1 to about 6 carbon atoms. The term "alkylthio" refers to an alkyl group, as defined above, having a sulfhydryl group attached thereto. Suitable alkylthio groups include groups having 1 to about 12 carbon atoms, or from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, or 1 to about 6 carbon atoms, e.g., methoxy, ethoxy, propoxy, tert-butoxy and the like. The terms "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, or from 1 to about 6 carbon atoms.

The term "alicyclic group" includes closed ring structures of three or more carbon atoms. Alicyclic groups include cycloparaffins or naphthenes which are saturated cyclic hydrocarbons, cycloolefins which are unsaturated with two or more double bonds, and cycloacetylenes which have a triple bond. They do not include aromatic groups. Examples of cycloparaffins include cyclopropane, cyclohexane, and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like. Suitable heteroaromatic and heteroalicyclic groups generally will have 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

The term "aromatic group" includes unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone, e.g., $C_1$-$C_{30}$ for straight chain or $C_3$-$C_{30}$ for branched chain. In certain embodiments, a straight chain or branched chain alkyl has 20 or fewer carbon atoms in its backbone, e.g., $C_1$-$C_{20}$ for straight chain or $C_3$-$C_{20}$ for branched chain, or 18 or fewer. In some embodiments, the cycloalkyls have from 4-10 carbon atoms in their ring structure, and more or have 4-7 carbon atoms in the ring structure. The term "lower alkyl" refers to alkyl groups having from 1 to 6 carbons in the chain, and to cycloalkyls having from 3 to 6 carbons in the ring structure.

Moreover, the term "alkyl" (including "lower alkyl") as used throughout the specification and claims includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl (benzyl).

The term "aryl" includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "amino," as used herein, refers to an unsubstituted or substituted moiety of the formula —NRaRb, in which Ra and Rb are each independently hydrogen, alkyl, aryl, or heterocyclyl, or Ra and Rb, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of Ra and Rb, is further substituted with an amino group.

As used herein, the term "polar surface functionality," refers to one or more polar functional groups or moieties that are present on the surface of stationary phase particles, which impart polarity on the surface of the particles and permit them to interact with polar analytes or molecules. Exemplary polar functional groups include hydroxyl, aldehyde; amine; alcohol; ester; ketone; acids; acid anhydrides; metal salts; heteroatoms such as nitrogen, oxygen, the halogens, boron, phosphorus or sulphur; carbonyl, imine, oxime, N-oxide, diol, carboxy, nitrile, azide, diazonium, isonitrile, cyanate, isocyanate, or the sulphur analogues of the aforementioned O-containing groups. In this context, the polar functional group or moiety is bonded directly to surface of the particles through the inorganic structure of the inorganic particles or through the organic or inorganic portions of the hybrid particles. For example, the direct binding of the polar functional groups to the inorganic structure of the inorganic particles or to the inorganic portion of the hybrid particles may be through the modified silane or silanol monomers or through a carbon-silicon bond. In these particles, one or more of the functional groups (e.g., silanol) may be capped or not.

Exemplary particles with polar surface functionality are cyano-bonded particles in which the group bound to the surface containing a cyanoalkyl group (e.g. —$(CH_2)$n-CN); diol-bonded particles in which the group bound to the surface containing a vicinal dihydroxyalkyl group (e.g., —$(CH_2)$n-CHOH—$CH_2$OH); amino-bonded particles in which the group bound to the surface containing an amino-alkyl group (e.g., —$(CH_2)$n-$NH_2$); or particles with free uncapped silanol groups and no additional polar groups being bound to the surface.

As used herein, the term "polar/non-polar surface functionality," as in particles having a polar/non-polar surface functionality, refers to particles that have a mixture of polar and non-polar functional groups on their surfaces. Exemplary non-polar functional groups are aliphatic groups. For example, the aliphatic group bound to the surface of the particles can be an alkyl chain between $C_1$ and $C_{18}$. The polar functional groups can be any of the ones described above. In an exemplary embodiment, a polar/non-polar surface functionality in particles refers to a mixture of non-polar functional groups and polar functional groups (e.g., hydroxyl groups or silanol groups that are uncapped) being present on the surfaces of the particles.

Exemplary hybrid particles with polar/non-polar surface functionality are alkyl-bonded particles in which the group bound to the surface contains an alkyl chain (usually between C1 and $C_{18}$); phenyl-bonded particles in which the group bound to the surface contains a phenyl group; or the like with the remaining functional (e.g., silanol) groups not being capped on the surface of the particles.

The "capped" stationary phase (or particle) (also known as "end-capped" stationary phase or material) is a bonded stationary phase (or particle) that has been treated with a second (usually less bulky) reagent, which is intended to react with remaining functional (e.g., silanol) groups which have not been substituted by the original reagent because of steric hindrance. Exemplary capping agents include, for example, tri organosiloxane.

As used herein, the term "analyte" or "solute" refers to a compound whose analytical levels or presence or absence in a sample is to be determined by the method and system of the subject technology.

As used herein, the term "sample" or "sample solution" refers to a material which one desires to test for the analytical levels or the presence or absence of steroids or steroid derivatives. The sample may be obtained from a living or non-living source. For example, the sample may be obtained from an animal tissue or bodily fluid or from plant. Without limitation, the sample may be obtained from leaves, seeds or other plant tissues, or from blood, plasma, urine, saliva or other animal tissues. The sample may also be obtained from a non-living object (e.g., drugs or active pharmaceutical ingredients) using extraction or leaching methods.

As used herein, the term "calibrators" refer to preparations of steroid mixtures with quantitatively known content that are used to prepare the necessary standards used to generate a calibration curve for steroid quantification.

As used herein, the term "controls" refers to preparations of steroid mixtures of known concentration, with steroid concentrations representing low, medium, and high levels of steroid concentrations within the calibration curve range. These are used to assess the analytical batch accuracy and acceptability.

As used herein, the term "tuning mixture" refers to a mixture of steroids in an appropriate solvent mixture used to optimize the performance of a mass spectrometer. A tuning mixture is often a mixture of known analytes with known concentrations that is used for tuning the mass spectrometer's performance.

As used herein, the term "internal standard" refers to a labeled steroid (e.g., isotopically or by fluorescence or the like) or closely related structural analogs of known concentration that can be added to the sample during preparation to increase the accuracy of steroid quantification.

As used herein, the term "derivatization reagents" refers to one or more compounds that can be reacted with the steroids or steroid derivatives to form a steroid-complex with increased mass spectroscopy sensitivity or improved chromatographic behavior relative to the underivatized steroid. Exemplary derivatization methods are alkylation, acylation and silylation, which are known in the art.

Unless otherwise indicated, all numbers expressing quantities such as flow volume or flow rate and so forth as used in the specification and claims are to be understood as being modified in all instances by the term "about." The term "about" as used herein in reference to quantitative measurements not including the measurement of the mass of a compound, refers to the indicated value plus or minus 10%.

Medical steroids are drugs that are structurally identical or similar to natural steroids produced by the body, and can function by binding to the same steroid receptor sites, turning that receptor on or off. Examples of this type of compounds include Prednisone, Oxandrolone, Stanozolol and Fludrocortisone. Because of their structural similarity to endogenous steroids, these compounds are amenable to separation using the $CO_2$-based system and method of the subject technology.

Figure 4:
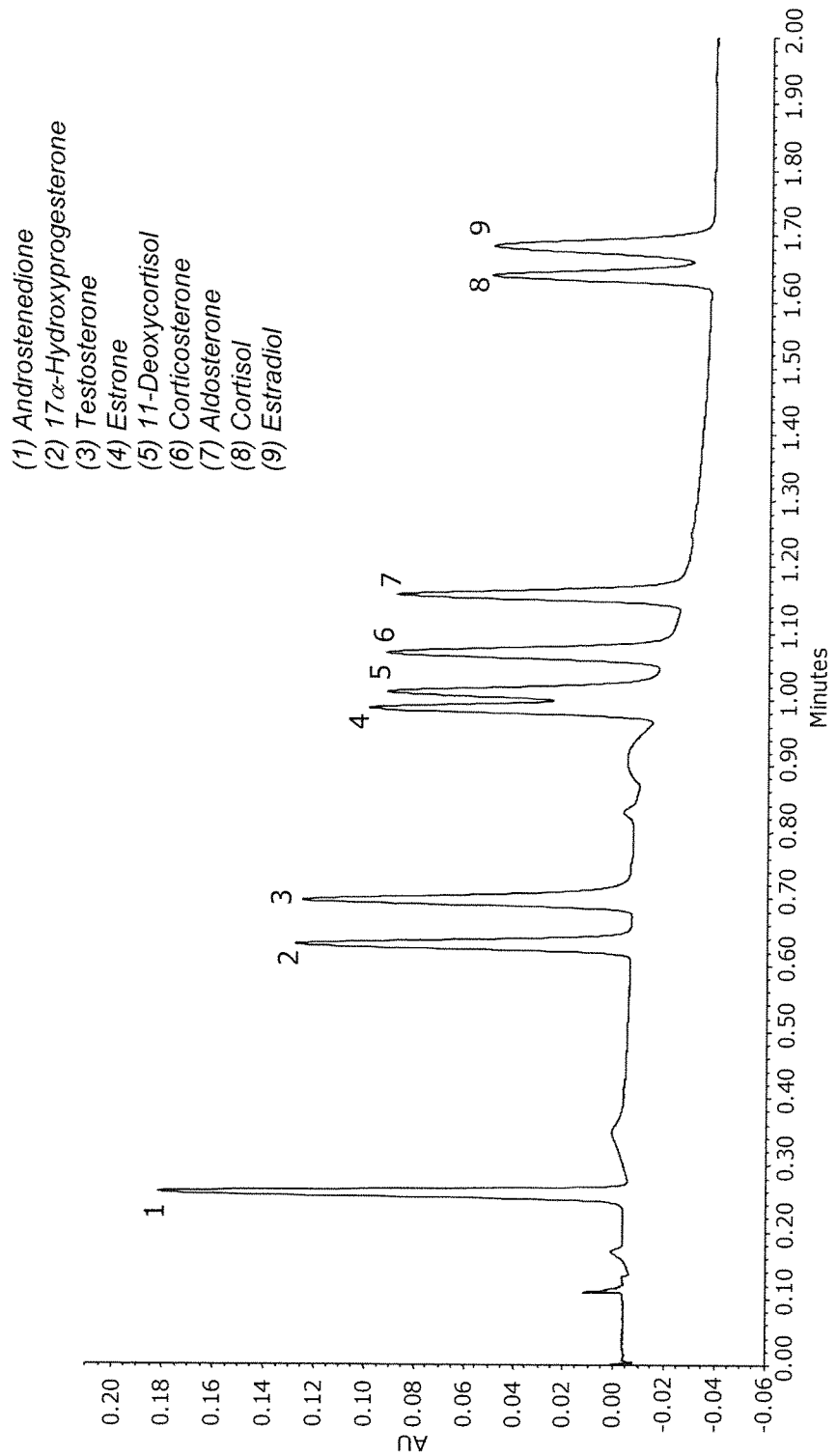
FIG. 4 is an exemplary chromatogram for nine steroids separated by the method and system of the subject technology. The chromatography column used for generating this result included solid stationary phase hybrid particles with a polar surface moiety (i.e., BEH 2-EP, hybrid particles with 2-ethylpyridine surface functionalities; Waters Corp., Milford, Mass.) and a mean particle size of 1.7 μm; the internal diameter of the column was 3.0 mm, with a column length of 50 mm. The detection was carried out with a UV detector (at 220 nm wavelength).
Figure 5:
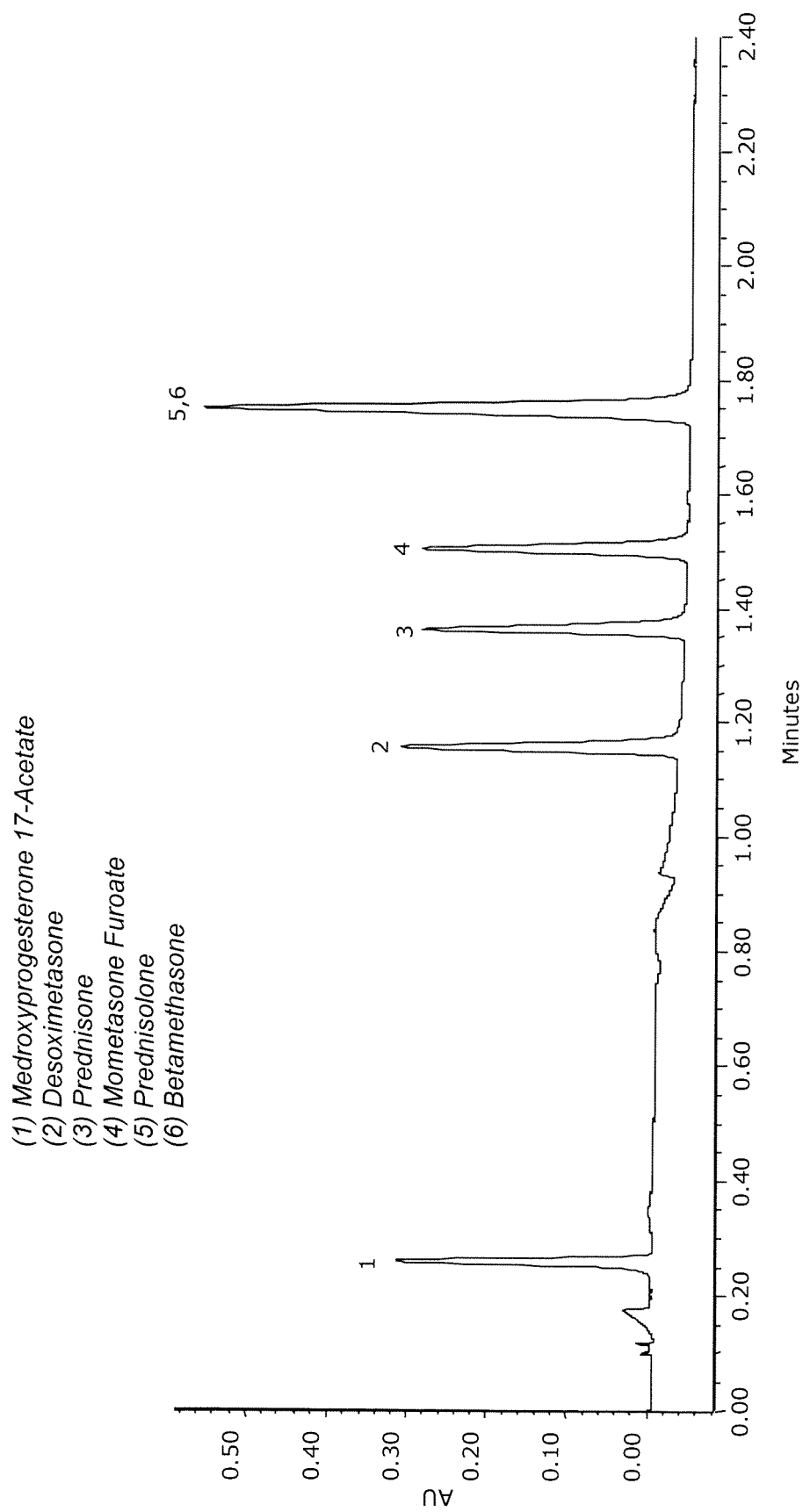
FIG. 5 is an exemplary chromatogram of six steroid derivatives separated by the method and system of the subject technology. The chromatography column used for generating this result included solid stationary phase hybrid particles with a polar surface moiety (i.e., BEH 2-EP; 1.7 μm (mean particle size), 3.0 mm (internal diameter), 50 mm (column length); Waters Corp. Milford, Mass.). The detection was carried out with a UV detector (at 220 nm wavelength).
Figure 19:
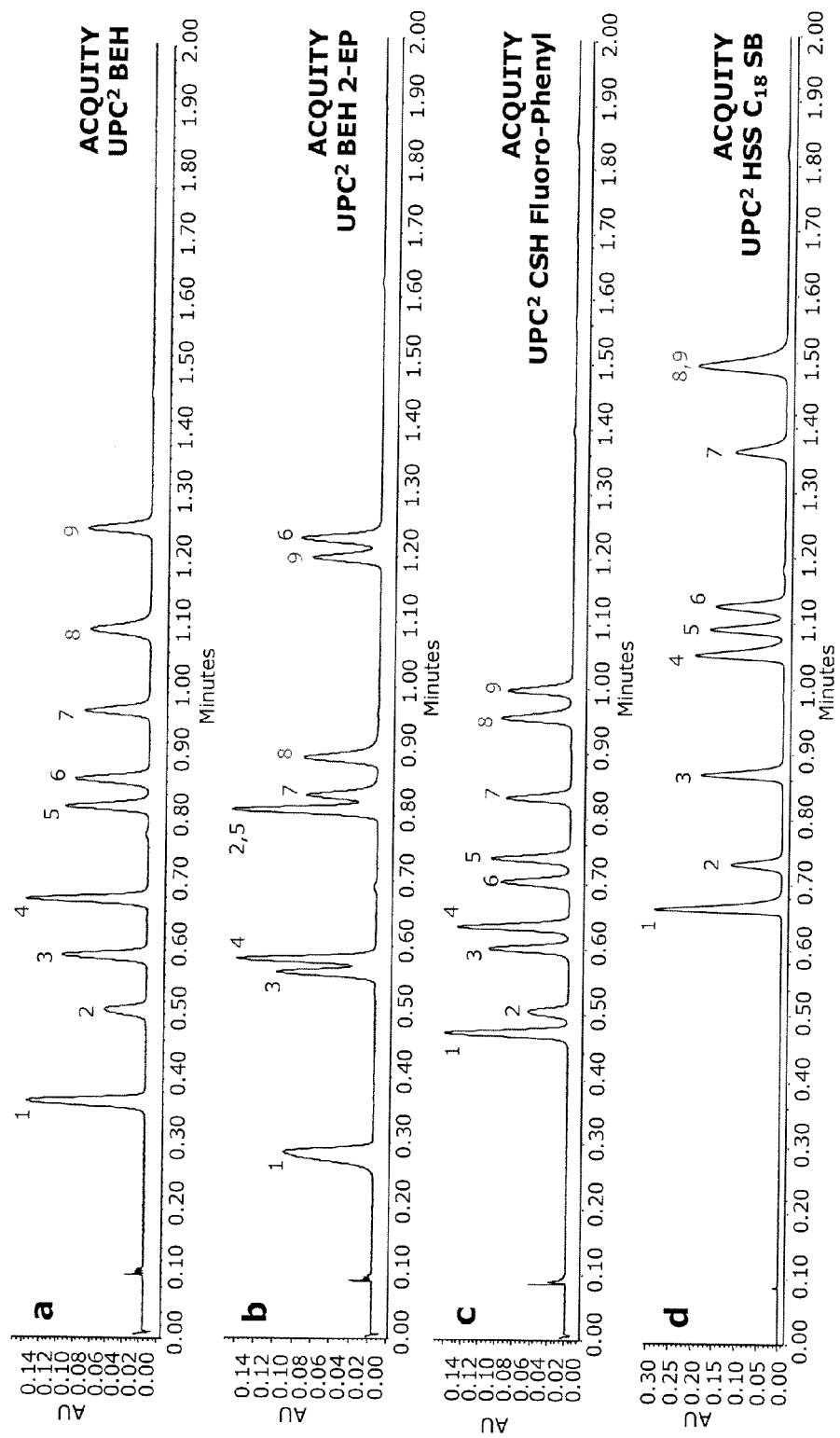
FIG. 19 is an exemplary illustration showing the $CO_2$ based chromatographic separation/UV detection of nine steroids using the following chromatography columns: BEH (a), BEH 2-EP (b), CSH Fluoro-Phenyl (c), and HSS C18 SB (d); all by Waters Corp., Milford, Mass. All columns were 1.7 μm, 3.0×50 mm configurations except for the HSS C18 SB which was a 1.8 μm particle size. Steroid compounds are androstenedione (1), estrone (2), 17a-OHP [17a-hydroxyprogesterone] (3), testosterone (4), 11-deoxycortisol (5), estradiol (6), corticosterone (7), aldosterone (8), and cortisol (9).

The unique speed and resolution provided by the $CO_2$-based system and method of the subject technology allows for conducting a steroid assay that is rapid enough to use for routine screening and diagnostic testing. In addition, because the system does not require great amounts of expensive mobile phase solvents, the cost of running such assays is substantially low compared with other chromatography methods. As discussed above, the subject technology is based, in part, on the discovery that the $CO_2$-based system and method of the subject technology provide a rapid separation of multiple closely related steroids, or steroids with similar molecular weights, in less than or about 2 minutes. As shown in FIGS. 4-5 and 19, even at such a short run time, the peaks associates with the steroids tested were surprisingly well-resolved with high signal to noise ratios. These results are attributable, in part, to the column chemistry, the stationary phase particle sizes used therein, and/or the $CO_2$-based system of the subject technology. Several of these attributes are discussed below in various embodiments.

Accordingly, in some embodiments, the subject technology relates to a method of detecting one or more steroids in a biological sample including the steps of: providing a biological sample including one or more steroids or steroid derivatives; placing said sample in a $CO_2$-based system with one or more features described herein; subjecting the one or more steroids to a separation column with one or more features described herein; eluting said one or more steroids with a mobile phase including $CO_2$ and at least one organic modifier to form one or more eluted steroids, and detecting said one or more eluted steroids with a suitable detection method.

The $CO_2$-Based System and Method of Use

FIG. 1 illustrates an exemplary and simplified diagram of the $CO_2$-based system of the subject technology. As shown, the $CO_2$-based system 100 includes a plurality of stackable modules including a solvent manager 110; a system manager 140; a sample manager 170; a column manager 180; and a detector module 190.

By way of illustration and not limitation, in some embodiments, the solvent manager 110 is comprised of a first pump 112 which receives carbon dioxide ($CO_2$) from $CO_2$ source 102 (e.g., a tank containing compressed $CO_2$). The $CO_2$ passes through an inlet shutoff valve 142 and a filter 144 in the system manager 140 on its way to the first pump 112. The first pump 112 can comprise one or more actuators each comprising or connected to cooling means, such as a cooling coil and/or a thermoelectric cooler, for cooling the flow of $CO_2$ as it passes through the first pump 112 to help ensure that the $CO_2$ fluid flow is deliverable in liquid form. In some cases, the first pump 112 comprises a primary actuator 114 and an accumulator actuator 116. The primary and accumulator actuators 114, 116 each include an associated pump head, and are connected in series. The accumulator actuator 116 delivers $CO_2$ to the system 100. The primary actuator 114 delivers $CO_2$ to the system 100 while refilling the accumulator actuator 116.

According to certain embodiments, the solvent manager 110 also includes a second pump 118 for receiving an organic co-solvent (e.g., methanol, ethanol, etc.) or modifier from a co-solvent source 104 and delivering it to the system 110. The second pump 118 can comprise a primary actuator 120 and an accumulator actuator 122, each including an associated pump head. The primary and accumulator actuators 120, 122 of the second pump 118 are connected in series. The accumulator actuator 122 delivers co-solvent to the system 100. The primary actuator 120 delivers co-solvent to the system 100 while refilling the accumulator actuator 122.

By way of illustration and not limitation, in some embodiments, transducers 124a-d are connected to outlets of the respective pump heads for monitoring pressure. The solvent manager 110 also includes electrical drives for driving the primary actuators 114, 120 and the accumulator actuators 116, 122. The $CO_2$ and co-solvent fluid flows are mixed at a tee 126 forming a mobile phase fluid flow that continues to an injection valve subsystem 200, which injects a sample slug for separation into the mobile phase fluid flow.

In some embodiments, the injection valve subsystem 200 is comprised of an auxiliary valve 220 that is disposed in the system manager 140 and an inject valve 240 that is disposed in the sample manager 170. The auxiliary valve 220 and the inject valve 240 are fluidically connected and the operations of these two valves are coordinated in such a manner as to reduce sample carry-over and system pressure perturbations occurring during injection. The reduced system pressure perturbations eliminate back flow in the column that may occur during injection and as the result of system pressure drops. The system manager 140 includes a valve actuator for actuating the auxiliary valve 220 and electrical drives for driving the valve actuations. Similarly, the sample manager 170 includes a valve actuator for actuating the inject valve and electrical drives for driving the valve actuations.

By way of illustration and not limitation, in some embodiments, from the injection valve subsystem 200, the mobile phase flow containing the injected sample slug continues through a separation column 182 in the column manager 180, where the sample slug is separated into its individual component parts. The column manager 180 comprises a plurality of such separation columns, and inlet and outlet switching valves 184, 186 for switching between the various separation columns.

After passing through the separation column 182, the mobile phase fluid flow continues on to a detector 192 (e.g., a flow cell/photodiode array type detector/mass spectrometer) housed within the detector module 190 then through a vent valve 146 and then on to a back pressure regulator 148 in the system manager 140 before being exhausted to waste 106. A transducer 149 is provided between the vent valve 146 and the back pressure regulator 148.

In some embodiments, the back pressure regulator 148 is adjustable to control or modify the system fluid pressure. This can allow the pressure to be changed from run to run. The properties of $CO_2$ affect how quickly compounds are extracted from the separation column 182, so the ability to change the pressure can allow for different separation based on pressure. In certain embodiments, the back pressure regulator 148 can be used to maintain the system pressure in the range of about 1000 psi to about 9000 psi, or in the range of about 1000 psi to about 6000 psi, or at any particular pressure within these ranges.

By way of illustration and not limitation, in some embodiments, also shown schematically in FIG. 1 is a computerized system controller 108 that can assist in coordinating operation of the $CO_2$-based system 100. Each of the individual modules 110, 140, 170, 180, 190 also includes its own control electronics, which can interface with each other and with the system controller 108 via an Ethernet connection 109. The control electronics for each module can include non-volatile memory with computer-readable instructions (firmware) for controlling operation of the respective module's components (e.g., the pumps, valves, etc.) in response to signals received from the system controller 108 or from the other modules. In some embodiments, each module's control electronics can also include at least one processor for executing the computer readable instructions, receiving input, and sending output. The control electronics can also include one or more digital-to-analog (D/A) converters for converting digital output from one of the processors to an analog signal for actuating an associated one of the pumps or valves (e.g., via an associated pump or valve actuator). The control electronics can also include one or more analog-to-digital (A/D) converters for converting an analog signal, such as from system sensors (e.g., pressure transducers), to a digital signal for input to one of the processors. In some embodiments, some or all of the various features of these control electronics can be integrated in a microcontroller.

Figure 2:
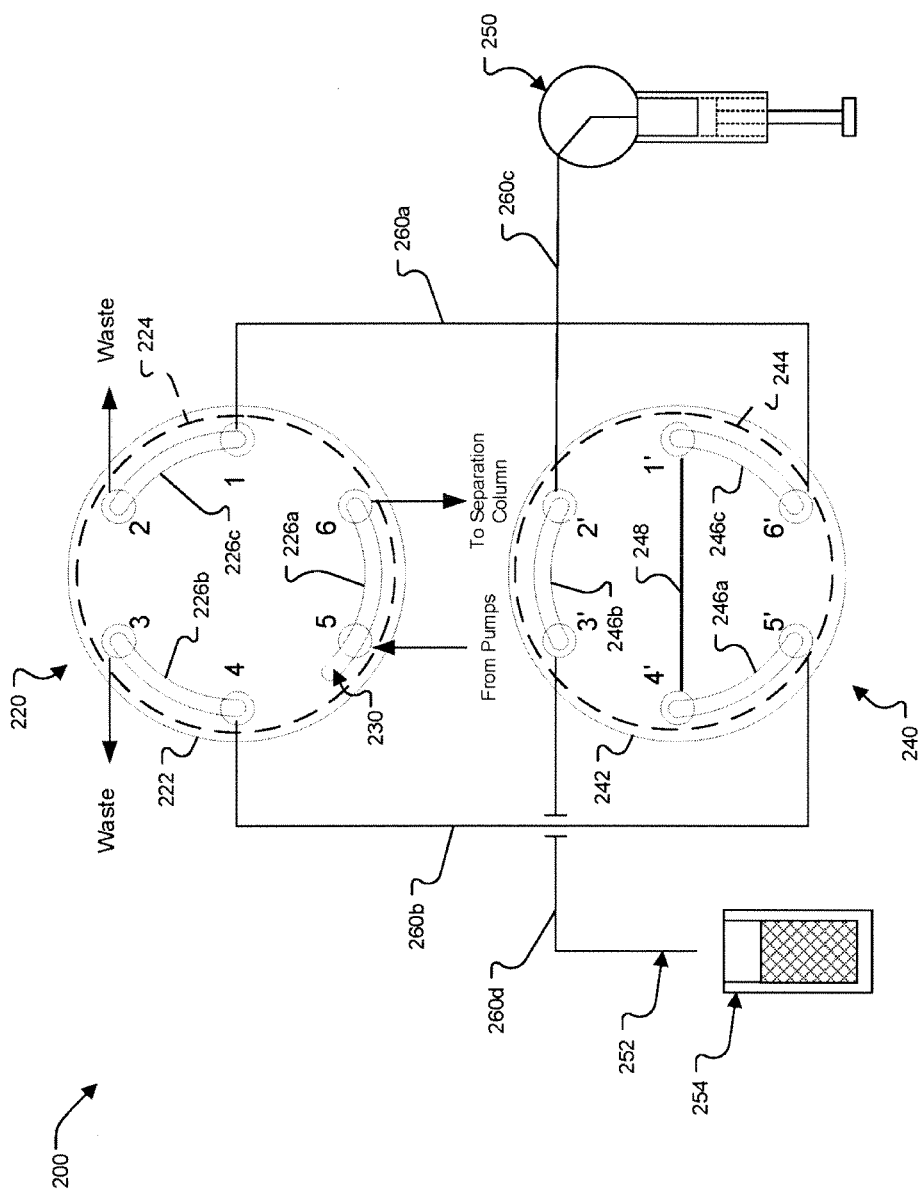
FIG. 2 is a schematic view of an exemplary injection valve for the $CO_2$-based system shown in FIG. 1.

In some embodiments, the injection valve subsystem 200 including the auxiliary valve 220 and the inject valve 240 is illustrated in FIG. 2. The auxiliary valve 220 is a rotary shear valve that includes an auxiliary valve stator 222 that has a plurality of ports, numbered 1 through 6 in FIG. 2, and an auxiliary valve rotor 224 that has a rotor interface, which includes three fluid conduits in the form of arcuate grooves 226a-c. When assembled, the rotor interface is urged into contact with the auxiliary valve stator 222, e.g., by pressure exerted on the auxiliary valve rotor 224 by a spring, to help ensure a fluid-tight seal therebetween. The ports 1-6 are configured to receive fittings (e.g., standard compression screw/ferrule type fittings) for coupling fluidic tubing to the auxiliary valve stator 222. In some embodiments, the auxiliary valve rotor 224 can be rotated to three discrete angular positions, relative to the auxiliary valve stator 222, to connect the rotor grooves 226a-c with different ones of the stator ports 1-6 to form different fluidic passageways. Notably, one of the grooves, groove 226a, includes an extended portion 230 which allows the auxiliary valve rotor 224 to be rotated to a position in which the groove 226a forms a fluidic pathway between stator ports 4 and 5, while ports 1-3 and 6 are dead ended.

By way of illustration and not limitation, in some embodiments, the inject valve 240 is another six-port rotary shear valve that includes an inject valve stator 242 having a plurality of ports, numbered 1' through 6' in FIG. 2, and an inject valve rotor 244. The inject valve rotor 244 has a rotor interface, which includes three fluid conduits in the form of arcuate grooves 246a-c. When assembled, the rotor interface is urged into contact with the inject valve stator 242, e.g., by pressure exerted on the inject valve rotor 244 by a spring, to help ensure a fluid-tight seal therebetween. In some embodiments, the ports 1'-6' are configured to receive fittings (e.g., standard compression screw/ferrule type fittings) for coupling fluidic tubing to the inject valve stator 242. Port 1' is fluidically connected to port 4' via a sample loop 248 (e.g., fluidic tubing external to the inject valve stator 242). Port 2' is fluidically connected to a metering syringe 250 and port 3' is connected to a needle 252. The metering syringe 250 and needle 252 are disposed within the sample manager 170 and are operable to aspirate sample from vials 254 also in the sample manager 170. Port 5' of the inject valve 240 is connected to port 4 of the auxiliary valve 220, and port 6' of the inject valve 240 is connected to port 1 of the auxiliary valve 220. The connections between port 2' and the syringe 250, between port 3' and the needle 252, between port 5' and port 4, and between port 6' and port 1 are made via the fluidic tubing 260a-d.

In some embodiments, the inject valve rotor 244 can be rotated to two discrete angular positions, relative to the inject valve stator 242, to connect the rotor grooves 246a-c with different ones of the stator ports 1'-6' to form different fluid passageways.

The coordinated operation of the auxiliary and inject valves 220, 240 helps to improve performance of the $CO_2$-based system 100 by reducing the amount of sample carry-over and can also help to reduce system pressure perturbations occurring during injection. As a result, the separation column 182 may be subjected to lower pressure pulses, potentially increasing the life of the column 182.

In short, during an injection, sample inside the sample loop 248 is brought online to the fluidic tubing 260a, 260b connecting the auxiliary and inject valves 220, 240 while mobile phase fluid comprising high pressure $CO_2$ flows directly from the pumps 112, 118 to the separation column 182 via the auxiliary valve 220. The auxiliary valve 220 then allows the fluidic tubing 260a, 260b, comprising gaseous $CO_2$ and sample, to fill and compress with the mobile phase fluid before introducing the fluid into the high pressure (e.g., about 1500 psi to about 9000 psi) stream. The combination of these two actions can help to reduce (e.g., eliminate) carry-over anomalies and system pressure pulses when introducing sample into the high pressure stream. The combination of these two actions can help to reduce (e.g., eliminate) carry-over anomalies and system pressure pulses when introducing sample into the high pressure stream. An exemplary process for operating the $CO_2$-based system of the subject technology is as follows.

Step 1: Sample Manager Setup

First, the sample manager 170 (FIG. 1) sets up internally by running various checks and setup procedures.

Step 2: De-Compress Sample Loop

At the start of an injection, the inject valve rotor 244 (FIG. 2) is in its inject position (from a previous injection), and the sample manager 170 triggers the auxiliary valve 220 to turn its rotor 224 (60 degrees counterclockwise) to its load position. This allows the sample loop 248 on the inject valve 240 and the fluidic tubing 260a, 260b connecting the auxiliary and inject valves 220, 240 to vent to atmosphere. At this time, the mobile phase fluid is permitted to flow directly from the pumps 112, 118 to the separation column 182 via the auxiliary valve 220. This pressurizes a flow path 262 (FIG. 1) between the auxiliary valve 220 and the separation column 182 to a system pressure of about 1500 psi to about 9000 psi.

Step 3: Aspirate Partial Loop with Needle Overfill (PLNO) Sample

Next, the sample manager 170 moves the needle 252 to a programmed vial position, aspirates an air gap, aspirates pre-sample buffer from the vial 254, aspirates the programmed amount of sample from the vial 254, aspirates post-sample buffer from the vial 254 (see FIG. 2), and then removes the needle 252 from the vial and returns it toward the inject port. A final air gap is aspirated in this position. Then, the sample manager metering syringe 250 meters the sample slug so that the injection volume is past port 2'. The syringe 250 then dispenses 0.5 µL to take out any compliance or backlash within the system.

Step 4: Load Sample into the Sample Loop

The inject valve rotor 244 is then moved (60 degrees clockwise) to place the inject valve 240 in its load position, with the sample loop 248 in fluidic communication with the meter and needle ports 2', 3' (FIG. 2), and the programmed sample volume is moved into the sample loop 248.

Step 5: Inject Sample into Fluidic Tubing

Within the sample manager 170, the inject valve rotor 244 is rotated (60 degrees counterclockwise) to the inject position, introducing sample into residual gaseous CO2 and programmed co-solvent from the previous injection in the fluidic tubing 260a, 260b connecting the auxiliary and injection valves 220, 240.

Step 6: Bring CO2 Online/Inject Sample into System

The sample manager 170 then triggers the auxiliary valve rotor 224 to turn (45 degrees clockwise) to place the auxiliary valve rotor 224 in its fill position to make the connection between ports 4 and 5 only. At this time, all other connections are dead ended. This action redirects the flow of mobile phase fluid comprising $CO_2$ and any programmed co-solvent from the pumps 112, 118 through the sample loop 248 and dead ends against port 1 of the auxiliary valve 220. The auxiliary valve rotor 224 remains in the fill position for a calculated pause time (based on mobile phase flow rate, sample loop 248 volume, and injection volume) until the fluidic tubing 260a, 260b and sample loop 248 are filled with liquid mobile phase comprising CO2 and any programmed co-solvent. During this time, the pressure in the flow path 262 between the auxiliary valve 220 and the separation column 182 remains substantially at system pressure (e.g., within 500 psi) due to the resistance to flow through the separation column 182 (FIG. 1). In this regard, the flow path 262 typically experiences a pressure drop of less than 500 psi while connections are dead ended.

Step 7: Inject Sample into System

The auxiliary valve rotor 224 is then rotated (an additional 15 degrees clockwise) to the inject position, completing all port connections. This action redirects the flow of mobile phase comprising high pressure $CO_2$ and any programmed co-solvent through the sample manager 170 and injects compressed sample into the high pressure system 100.

Step 8: Wash the Needle

With the auxiliary and inject valve rotors 224, 244 in their respective inject positions, the sample manager 170 washes the outside and inside of the needle 252 after sample is injected. The wash syringes dispense a programmed amount of strong and weak washes through the inject valve 240 and out through the needle 252.

Figure 3:
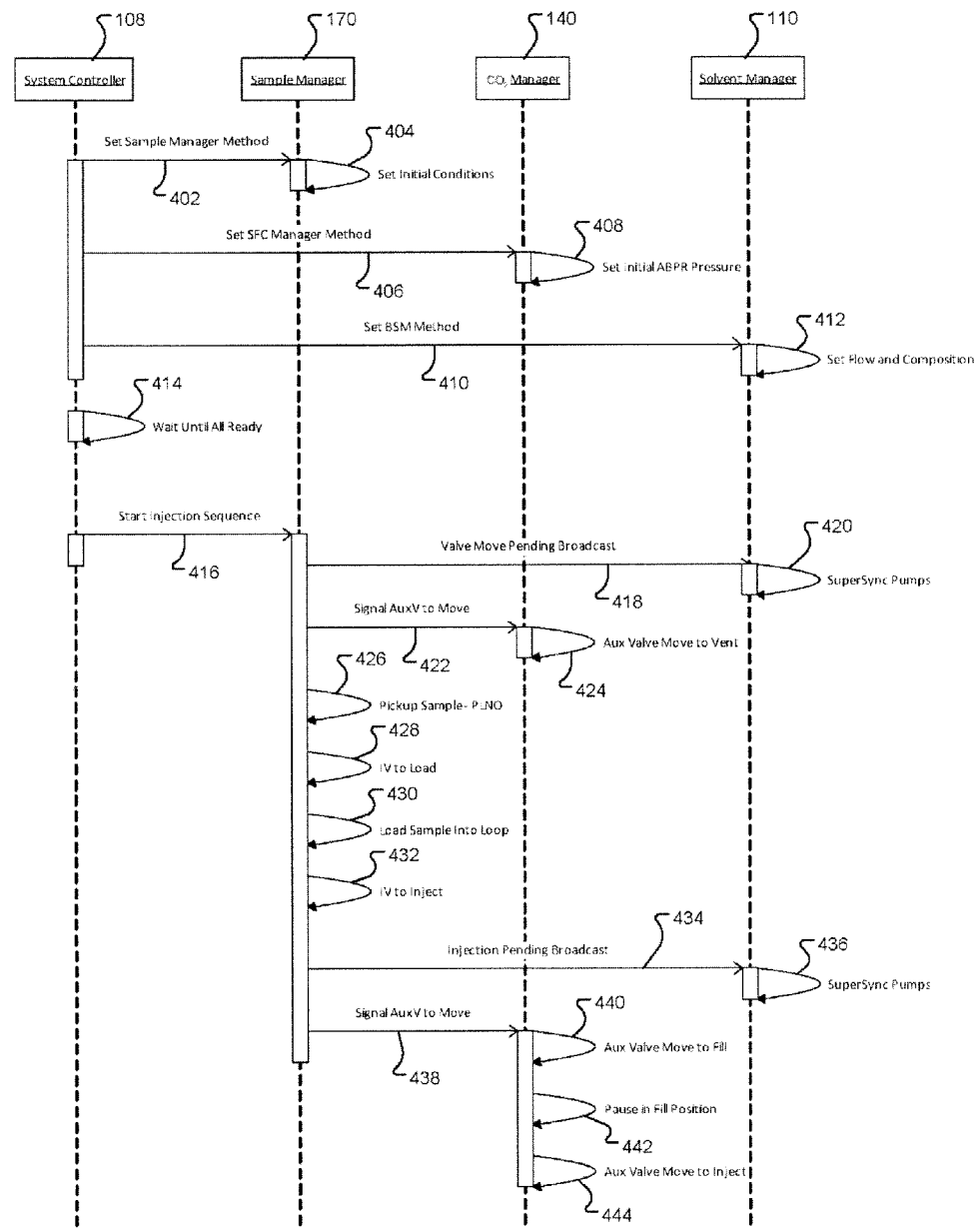
FIG. 3 is an exemplary diagram showing a software timing mode for developing an injection sequence in the $CO_2$-based system of the subject technology.

By way of illustration and not limitation, FIG. 3 depicts an exemplary software timing diagram used to develop the injection sequence, according to some embodiments of the subject technology. With reference to FIG. 3, the system controller 108 signals (402) the sample manager 170, via the Ethernet connection, triggering the sample manager 170 to rotate (404) the inject valve rotor 244 to its inject position. The system controller 108 also signals (406) the system manager 140 to set (408) the back pressure regulator 148 to provide the desired pressure setting. Finally, the solvent manager 110 is triggered (410) by the controller 108 to set (412) the flow and composition of the mobile phase solvent. The system controller 108 waits (414) until the sample manager 170, system manager 140, and solvent manager 110 have performed their respective tasks and are ready to perform a sample injection.

Then, the system controller 108 signals (416) the sample manager 170 to start the injection sequence. In response, the sample manager 170 signals (418) the solvent manager 110 to synchronize (420) the pumps (positioning plungers within the actuators in a predetermined start point position). The sample manager 170 then signals (422) the system manager 140 to move (424) the auxiliary valve rotor 224 to its load position. Next, the sample manager 170 executes the step of aspirating the PLNO sample (426), and, then, drives (428) the inject valve rotor 244 to its load position. After sample is loaded (430) into the sample loop 248, the sample manager 170 drives (432) the inject valve to the inject position. The sample manager 170 then signals (434) the solvent manager 110 to again synchronize (436) the actuator plungers.

Finally, the sample manager 170 signals (438) the system manager 140 to execute the final movements of the auxiliary valve rotor 224. In response, the system manager 140 drives (440) the auxiliary valve rotor 224 to its fill position, and then pauses (442) it in the fill position (to fill and pressurize the fluidic tubing 260a, 260b with liquid mobile phase comprising CO2 and programmed co-solvent). Then, the system manager 140 drives (444) the auxiliary valve rotor 224 to its inject position (for injection of the sample into high pressure system).

In some embodiments, the system pressure of the $CO_2$-based system of the subject technology, which is the pressure of the liquid as it exits the pump, is from about 4000 psi to about 9000 psi. In an embodiment, the system pressure is any pressure between the ranges of about 1000 psi to about 9000 psi or about 1000 psi to about 6000 psi. In some embodiments, the system pressure controller of the $CO_2$- based system of the subject technology provides and maintains steady pressure levels, and provides accurate and reproducible pressure gradients.

In some embodiments, the pressure at the exit of the system, as controlled by the automated backpressure regulator (ABPR) in the $CO_2$-based system of the subject technology is from about 1000 psi to 9000 psi. In an embodiment, the backpressure is any pressure between the ranges of about 1000 psi to about 9000 psi or about 1000 psi to about 6000 psi. In another embodiment, the ABPR is set at 1700 psi, 2200 psi, 2500 psi, 2900 psi, 3200 psi, 3500 psi. In some embodiments, the ABPR of the $CO_2$-based system of the subject technology provides steady pressure levels and improved pressure gradients.

In some embodiments, the pre-column mobile phase dwell volume of the $CO_2$-based system of the subject technology is about 75 μL to about 500 μL. The pre-column mobile phase dwell volume is the volume of mobile phase present in a fluidic connection or piping between a junction at which the $CO_2$ and the modifier are mixed and the head of the chromatography column. In an embodiment, the pre-column mobile phase dwell volume is about 100 μL, or about 150 μL, or about 200 μL, or about 250 μL, or about 300 μL, or about 320 μL, or about 350 μL, or about 400 μL or about 450 μL, or any volumes therebetween.

In some embodiments, the internal diameter of the fluidic connection that holds the pre-column mobile phase dwell volume is about 50 μm to about 400 μm. In some embodiments, the internal diameter of the fluidic connection that holds the pre-column mobile phase dwell volume is about 75 μm, or about 100 μm, or about 130 μm, or about 150 μm, or about 200 μm, or about 250 μm, or about 300 μm, or about 350 μm, or about 375 μm, or any lengths therebetween.

In some embodiments, the post-column mobile phase dwell volume of the $CO_2$-based system of the subject technology is about 10 μL to 450 μL. The post-column mobile phase dwell volume is the volume of mobile phase present in a fluidic connection or piping between the end of the column and the detector. In an embodiment, the post-column mobile phase dwell volume is about 10 μL, about 20 μL, about 30 μL, about 50 μL, about 90 μL, or about 120 μL, or about 150 μL, or about 200 μL, or about 250 μL, or about 300 μL, or about 350 μL, or about 400 μL or any volumes therebetween.

In some embodiments, the internal diameter of the fluidic connection that holds the post-column mobile phase dwell volume is about is about 50 μm to about 400 μm. In some embodiments, the internal diameter of the fluidic connection that holds the post-column mobile phase dwell volume is about 75 μm, or about 100 μm, or about 130 μm, or about 150 μm, or about 200 μm, or about 250 μm, or about 300 μm, or about 350 μm, or about 375 μm, or any lengths therebetween.

In some embodiments, the volume of the sample needed to be injected to the $CO_2$-based system of the subject technology is from about 0.1 μL to 20 μL, or any particular volume in between this range. For example, in an embodiment, the sample volume injected is 1 μL. However, those of skill in the art appreciate that the volume of sample to be injected depends primarily on the concentration of the analytes in that sample and also on what type of detection method being used. For example, if MS (Mass Spectroscopy) is the detection method used in tandem with the $CO_2$-based system of the subject technology, smaller injection volumes are typically required. In some embodiments, the $CO_2$-based system of the subject technology when in tandem with an MS/MS can facilitate detection of analytes in picogram (pg, one trillionth ($10^{-12}$) of a gram) ranges.

In some embodiments, the temperature fluctuations in the pumping systems which may result in system pressure fluctuations are reduced or eliminated, which leads to a reduced baseline noise of chromatograms generated by the $CO_2$-based system and method of the subject technology.

Alternatively or in addition, the $CO_2$-based system of the subject technology minimizes the consumption of mobile phase solvents (e.g. methanol, acetonitrile) thereby generating less waste for disposal and reducing the cost of analysis (by more than 100 fold, in some cases) per sample.

Column Chemistry

In various embodiments, the solid stationary phase of the chromatography columns of the $CO_2$-based system of the subject technology includes porous inorganic or inorganic/organic hybrid particles with the mechanical stability and structural integrity required to withstand the operating pressures of the system.

Inorganic particles suitable for use in the system and method of the subject technology include silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof. In some embodiments, such inorganic particles may have no surface modifications. For example, without surface modifications, silica is characterized by the presence of silanol groups on its surface. In some other embodiments, the inorganic particles, e.g., silica, may have been surface modified. For example, silica can be surface modified or derivatized with an organic polar or non-polar functional group such as butyl ($C_4$), octyl ($C_8$), octadecyl ($C_{18}$), $C_{30}$, phenyl, amino, cyano, etc. An exemplary and suitable commercially available column that includes such particle is, for example, the ACQUITY UPC$^2$ HSS $C_{18}$ SB column by Waters Corporation, Milford, Mass.

Hybrid particles suitable for use in the system and method of the subject technology include an inorganic portion such as, e.g., alumina, silica, titanium or zirconium oxides, or ceramic material; and an organic portion bonded to one or more atoms of the inorganic portion. Exemplary hybrid materials are disclosed in U.S. Pat. No. 4,017,528, the text of which is incorporated herein by reference.

In some embodiments, the organic portion of the hybrid particles is a $C_1$-$C_{18}$ aliphatic or aromatic moieties (which may additionally be substituted with alkyl, aryl, cyano, amino, hydroxyl, diol, nitro, ester, ion exchange or embedded polar functionalities) or a substituted or unsubstituted $C_1$-$C_{18}$ alkylene, alkenylene, alkynylene or arylene moiety.

In one embodiment where the inorganic portion is silica; and the hybrid silica particles refer to particles having the formula $SiO_2/(R^2_p R^4_q SiO_t)_n$ or $SiO_2/[R^6(R^2_r SiO_t)_m]_n$ (disclosed in U.S. Pat. Nos. 7,919,177; 7,223,473, and 6,686,035, each of which is hereby incorporated herein by reference) wherein $R^2$ and $R^4$ are independently $C_1$-$C_{18}$ aliphatic or aromatic moieties (which may additionally be substituted with alkyl, aryl, cyano, amino, hydroxyl, diol, nitro, ester, ion exchange or embedded polar functionalities), $R^6$ is a substituted or unsubstituted $C_1$-$C_{18}$ alkylene, alkenylene, alkynylene or arylene moiety bonded to one or more silicon atoms or bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, or alternatively, 0.1 to 1, or alternatively 0.2 to 0.5. $R^2$ may be additionally substituted with a functionalizing group R.

The functionalizing group R includes organic functional groups which impart a certain chromatographic functionality to a chromatographic stationary phase, including, e.g., octadecyl ($C_{18}$) or phenyl. Such functionalizing groups are present in, e.g., surface modifiers such as disclosed herein which are attached to the base material, e.g., via derivatization or coating and later crosslinking, imparting the chemical character of the surface modifier to the base material. In an embodiment, such surface modifiers have the formula $Z_a(R')_bSi$—R, where Z=Cl, Br, I, C1-C5 alkoxy, dialkylamino, e.g., dimethylamino, or trifluoromethanesulfonate; a and b are each an integer from 0 to 3 provided that a+b=3; R' is a C1-C6 straight, cyclic or branched alkyl group, and R is a functionalizing group. R' may be, e.g., methyl, ethyl, propyl, isopropyl, butyl, t-butyl, sec-butyl, pentyl, isopentyl, hexyl or cyclohexyl; in an embodiment, R' is methyl.

The porous inorganic/organic hybrid particles possess both organic groups and silanol groups which may additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later crosslinking, imparting the chemical character of the surface modifier to the base material. In one embodiment, the organic groups of the hybrid particle react to form an organic covalent bond with a surface modifier. The surface modifiers can form an organic covalent bond to the particle's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds.

In some embodiments, the solid stationary phase of the chromatography column of the subject technology includes a monolith, particles, porous particles, and/or superficially porous particles. Particles can be spherical or non-spherical. The solid stationary phase can include silica, inorganic silica, and/or metal oxide. In some embodiments, the column is equipped with one or more frits to contain the stationary phase material. In embodiments in which the stationary phase material is monolithic, the housing may be used without the inclusion of one or more frits.

The solid stationary phase includes, for example, particles having a mean size within the range of about 0.5-3.5 microns, though a smaller or larger size could be selected if appropriate for a desired application. In various examples, the mean particle size is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, or 3.5 microns. In general, particle size can be selected in view of the desired pressure and/or flow rate. For example, larger particle size can be used to achieve consistent pressure from a column head to an end during high pressurized digestion. Alternatively, smaller particle sizes result in higher flow rates, higher efficiency, which yield faster, more sensitive separations. The solid stationary phase can include pores having a mean pore volume within the range of 0.1-2.5 cm/g. In various examples, the mean pore volume is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 cm/g. In some embodiments, porous particles may be advantageous because they provide a relatively large surface area (per unit mass or column volume) for protein coverage at the same time as the ability to withstand high pressure.

The solid stationary phase can include pores having a mean pore diameter within the range of 100-1000 Angstroms. For example, the mean pore diameter can be about 100, 200, 300, 400, 500, 600, 700, 800, 900, 1000 Angstroms or any value or range therebetween.

In certain embodiments, said chromatography column of the subject technology, includes (a) a column having a cylindrical interior for accepting a packing material, and (b) a packed chromatographic bed comprising a porous material comprising an organosiloxane/SiO2 material having the formula $SiO_2/(R^2_pR^4_qSiO_t)_n$ or $SiO_2/[R^6(R^2_rSiO_t)_m]_n$, as described above, wherein R2 and R4 are independently C1-C18 aliphatic, styryl, vinyl, propanol, or aromatic moieties, R6 is a substituted or unsubstituted $C_1$-$C_{18}$ alkylene, alkenylene, alkynylene or arylene moiety bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, said porous hybrid silica chromatographic matrix having a chromatographically-enhancing pore geometry and average pore diameters of about 100 to 300 Å.

In an embodiment, the solid stationary phase particles have surface modification(s). In another embodiment, the particles have been surface modified by a surface modifier selected from the group consisting of an organic group surface modifier, a silanol group surface modifier, a polymeric coating surface modifier, and combinations thereof. In another embodiment, the surface modifier has the formula $Z_a(R')_bSi$—R, where Z=Cl, Br, I, $C_1$-$C_5$ alkoxy, dialkylamino or trifluoromethanesulfonate; a and b are each an integer from 0 to 3 provided that a+b=3; R' is a $C_1$-$C_6$ straight, cyclic or branched alkyl group, and R is a functionalizing group.

The functionalizing group R may include alkyl, alkenyl, alkynyl, aryl, cyano, amino, diol, nitro, cation or anion exchange groups, or alkyl or aryl groups with embedded polar functionalities. Examples of suitable R functionalizing groups include $C_1$-$C_{30}$ alkyl, including $C_1$-$C_{20}$, such as octyl ($C_8$), octadecyl ($C_{18}$), and triacontyl ($C_{30}$); alkaryl, e.g., $C_1$-$C_4$-phenyl; cyanoalkyl groups, e.g., cyanopropyl; diol groups, e.g., propyldiol; amino groups, e.g., aminopropyl; and alkyl or aryl groups with embedded polar functionalities, e.g., carbamate functionalities such as disclosed in U.S. Pat. No. 5,374,755, the text of which is incorporated herein by reference. In an embodiment, the surface modifier is an organotrihalosilane, such as octyltrichlorosilane or octadecyltrichlorosilane. In another embodiment, the surface modifier may be a halopolyorganosilane, such as octyldimethylchlorosilane or octadecyldimethylchlorosilane.

In another embodiment, the hybrid particle's organic groups and silanol groups are both surface modified or derivatized. In another embodiment, the particles are surface modified by coating with a polymer. In certain embodiments, surface modification by coating with a polymer is used in conjunction with silanol group modification, organic group modification, or both silanol and organic group modification.

Polymer coatings are known in the literature and may be provided generally by polymerization or polycondensation of physisorbed monomers onto the surface without chemical bonding of the polymer layer to the support (type I), polymerization or polycondensation of physisorbed monomers onto the surface with chemical bonding of the polymer layer to the support (type II), immobilization of physisorbed prepolymers to the support (type III), and chemisorption of presynthesized polymers onto the surface of the support (type IV). See, e.g., Hanson et al., J. Chromat. A656 (1993) 369-380, the text of which is incorporated herein by reference. As noted above, coating the hybrid material with a polymer may be used in conjunction with various surface modifications described in U.S. Pat. Nos. 7,919,177; 7,223, 473, and 6,686,035, each of which is hereby incorporated herein by reference. Additional inorganic/organic hybrid particles are disclosed in WO2010141426, which is hereby incorporated herein by reference.

Exemplary and/or suitable commercially available columns that include such inorganic/organic hybrid particles include, for example, the ACQUITY UPC$^2$ BEH 2-EP, or ACQUITY UPC$^2$ CSH C18 SB, both from Waters Corporation, Mildford, Mass.

In an exemplary embodiment, the particles used in the separation columns of the $CO_2$-based system of the subject technology have the following specifications:

| Chemistry | Particle Shape | Particle Size (μm) | Pore Size (Å) | Surface Area (m$^2$/g) | Carbon Load (%) | Endcapped |
|---|---|---|---|---|---|---|
| Hybrid particles with a polar surface functionality (e.g., 2-ethylpridine) | Spherical | 1.7, 3.5 | 135 | 185 | 9 | No |
| Hybrid particles with surface silanol groups but no additional surface functionality | Spherical | 1.7, 3.5 | 135 | 185 | N/A | N/A |
| Hybrid particles with surface modification/polymer coating (e.g., flourphenyl) | Spherical | 1.7, 3.5 | 135 | 185 | 10 | No |
| Inorganic silica particles with a surface functionality (e.g., $C_1$-$C_{18}$) | Spherical | 1.7, 3.5 | 100 | 230 | 8 | No |

In some embodiments, the depending on the complexity and nature of the sample components, the separation is accomplished using a hybrid material stationary phase surface modified with an alternate ligand (polar, non-polar, or ionic), or one with no additional surface modification at all. Additionally, the separation could be achieved on various particles sizes below 5 μm in diameter.

In some embodiments, the internal diameter (ID) of the chromatography column of the subject technology is between about 1 mm to about 5 mm, or between about 2 mm to about 4 mm. In an embodiment, the ID of the column is about 2 mm, or about 3 mm, or about 4 mm.

In some embodiments, the length of the chromatography column of the subject technology is between about 30 mm to about 200 mm or between about 50 mm to about 150 mm. In an embodiment, the length of the chromatography column is about 50 mm. In another embodiment, the length of the chromatography column is about 150 mm.

In some embodiments, depending on the column dimension chosen and optimization necessary, the flow rate of the mobile phase is set between about 0.1 mL/min to about 4 mL/min, or any intervals there between, e.g., between about 0.5 mL/min to about 3.5 mL/min, with a backpressure regulator setting of about 1000-9000 psi, or about 1000-6000 psi, or about 1000-4000 psi or any pressures therebetween.

In certain other embodiments, temperature at which the chromatography column operates is adjusted to optimize the analyte separations with a practical working range of about 5° C. to about 85° C., or any specific temperature within this range. In an embodiment, the column temperature ranges from about 20° C. to about 70° C. In another embodiment, the column temperature is kept at about 20° C. or at about 85° C. or at any specific temperature between about 5° C. to about 85° C.

Mobile Phase Solvent

In some embodiments, the method of the subject technology relates to method of detecting the presence or absence or levels of an analyte or a solute (e.g., steroids) in a mixture. Thus, according to certain embodiments of the subject technology, a solution having an analyte is contacted with a porous material of the separation column under conditions that allow for sorption of the analyte to the porous material. The analyte can be, e.g., any steroid or steroid derivative having a hydrophobic, hydrophilic, or ionic interaction or a combination of two or three of these interactions. The porous material having the sorbed analyte is eluted with a solvent under conditions so as to desorb the analyte from the porous material. The level of the desorbed analyte (e.g., eluted steroid) present in the solvent eluted from the separation column after the elution can then be detected using a suitable detection method.

In general, liquid $CO_2$ is used as the main mobile phase solvent of the subject technology to desorb the solute(s). In some embodiments, the liquid $CO_2$ is in a supercritical state. In some embodiments, the liquid $CO_2$ is in a subcritical state. In some embodiments, the physical state of the liquid $CO_2$ changes between supercritical and subcritical or vice versa. Due to its miscibility, the $CO_2$ solvent can be combined with one or more modifiers (co-solvents) for more effective desorption or elution of the analytes from the chromatography column.

In some embodiments, suitable modifiers to be combined with the $CO_2$ mobile phase include, e.g., polar water-miscible organic solvents, such as alcohols, e.g., methanol, ethanol or isopropanol, acetonitrile, acetone, and tetrahydrofuran, or mixtures of water and any of these solvents. In other embodiments, the modifiers include, e.g., non-polar or moderately polar water-immiscible solvents such as pentane, hexane, heptane, xylene, toluene, dichloromethane, diethylether, chloroform, acetone, dioxane, THF, MTBE, ethylacetate or DMSO. Mixtures of these modifiers are also suitable. In some embodiments, modifiers or modifier mixtures must be determined for each individual case. A suitable modifier can be determined by one of ordinary skill in the art without undue experimentation, as is routinely done in chromatographic methods development.

In one embodiment, the ratio of a modifier to $CO_2$ (v/v) is between about 0.0001 to 1 to about 1 to 1. In another embodiment, this ratio of modifier to $CO_2$ (v/v) is between about 0.001 to 1 to about 1 to 1, or any ratios in between. In certain embodiments, the amount of the modifier added to $CO_2$ is constant or changes in a gradient mode (increasing or decreasing), or is a combination of both, during the elution period. In certain other embodiments, the modifier is added to the $CO_2$ mobile phase at a constant rate of, for example, 8%, or 10%, or 20%, or 25% over the elution period.

In some embodiments the modifier is added, in an increasing gradient mode, from about 0% to 50% (v/v of $CO_2$), or from about 8% to 33%, or from about 6% to 35%, or from about 4% to 37%, or from about 9% to 40% (v/v of $CO_2$), or from about 8% to 27%, or from about 11%-30%, or any other intervals within the 0% to 50% (v/v of $CO_2$) range, over the elution period.

In some embodiments the modifier is added, in a decreasing gradient mode, from about 50% to 0% (v/v of $CO_2$), or from about 33% to 8%, or from about 35% to 6%, or from about 37% to 4%, or from about 40% to 9% (v/v of $CO_2$), or from about 27% to 8%, or from about 30%-11%, or any other intervals within the 50% to 0% (v/v of $CO_2$) range, over the elution period.

In some embodiments, the modifier is added to the $CO_2$ mobile phase in a gradient of 0% to about 50% (v/v of CO2) (or any ascending percentage range within 0% to 50%) in about 2 min (or any fraction of time within this range) with a hold period at a constant modifier percentage at the beginning, at the end or at anytime during the elution period. For example, in an embodiment, the hold period is for about 0.1 to 1 min (or any fraction of time within this range) at constant modifier volume of, e.g., 5%, 10%, 15%, 20%, 30%, 40% (v/v of $CO_2$) or more. In some embodiments, the modifier is added in gradients of 0% to about 70% or less (v/v of $CO_2$), 0% to about 50% or less (v/v of $CO_2$), or 0% to about 30% or less (v/v of $CO_2$) over the elution period.

In some embodiments, the modifier is added to the $CO_2$ mobile phase in a gradient of about 50% to 0% (v/v of $CO_2$) (or any descending percentage value within 50% to 0%) in about 2 min (or any fraction of time within this range) with a hold period at a constant modifier percentage at the beginning, at the end or at anytime during the elution period. In some embodiments, the modifier can be added in gradient of about 70% to 0% or more (v/v of $CO_2$), about 50% to 0% or more (v/v of $CO_2$), or about 30% to 0% or more (v/v of $CO_2$). In an embodiment, the modifier is added to $CO_2$ with a gradient of 40% to about 10% in 1.5 min and a hold at 25% for 0.5 minute.

In some embodiments, depending on the column dimension chosen and optimization necessary, the flow rate of the mobile phase is set between about 0.1 mL/min to 4 mL/min during the elution period. In an embodiment, the flow rate increases in a gradient of about 0.5 mL/min to 4.0 mL/min, or any intervals therebetween. In another embodiment, the flow rate decreases in a gradient of 4.0 mL/min to 0.5 mL/min, or any intervals therebetween. In another embodiment, the flow rate remains constant at, for example, about 0.8 mL/min, or about 2 mL/min or about 3.5 mL/min.

In some embodiments, depending on the nature of the steroids or steroid derivatives being analyzed or their modifications, the mobile phase further includes one or more additives for optimizing the separation. In an embodiment, one or more additives including, e.g. formic acid, ammonium acetate, isopropyl amine, diethyl amine, ammonium hydroxide or the like, which are added to the mobile phase at a concentration range of about 0.5% to 5% (v/v of modifier) or any specific percentage within this range. In an embodiment, the additive is added at a constant amount of 3% (v/v of modifier) over the elution period.

In some embodiment, depending on the polarity of the steroid or steroid derivatives, the gradient duration ($t_g$) of the mobile phase is varied between about 0.1 min to 12 min or any specific period within this range. In an embodiment, $t_g$ is about 1 min, or about 2 min, or about 3 min, or about 5 min, or about 7 min.

In some embodiments, the entire elution period is less than or equal to about 12 min, or less or equal to than about 8 min, or less than or equal to about 5 min, or less than or equal to about 4 min, or less than or equal to about 3 min, or less than or equal to about 2 min, or less than or equal to about 1.5 min.

Due to the reason that supercritical and/or liquid $CO_2$ is miscible with the entire eluotropic series, various polar and non-polar modifiers can be added to $CO_2$ to facilitate desorption of a wide variety of analytes or solutes. A related advantage of the $CO_2$-based system of the subject technology is its compatibility with a wide range of sample solutions and solvents.

Sample Preparation

A sample for analysis can be any sample, from biological and non-biological sources. For example, a sample may be a food (e.g., meat, dairy, or vegetative sample) or beverage sample (e.g., orange juice or milk). A sample may be a pharmaceutical formulation or a nutritional or dietary supplement. In certain cases, a sample can be a biological sample, such as a tissue (e.g., adipose, liver, kidney, heart, muscle, bone, or skin tissue) or biological fluid (e.g., blood, serum, plasma, urine, lachrymal fluid, cerebrospinal fluid, synovial fluid or saliva) sample. The biological sample may be from a mammal. A mammal may be a human, dog, cat, primate, rodent, pig, sheep, cow, or horse.

A sample can be treated to remove components that could interfere with the detection technique such as a mass spectrometry technique. A variety of extraction and purification techniques known to those having skill in the art can be used based on the sample type. Solid and/or tissue samples can be grinded and extracted to free the analytes of interest from interfering components. In such cases, a sample can be centrifuged, filtered, and/or subjected to chromatographic techniques to remove interfering components (e.g., cells or tissue fragments). In yet other cases, reagents known to precipitate or bind the interfering components can be added. For example, whole blood samples can be treated using conventional clotting techniques to remove red and white blood cells and platelets. A sample can be de-proteinized. For example, a plasma sample can have serum proteins precipitated using conventional reagents such as acetonitrile, KOH, NaOH, or others known to those having ordinary skill in the art, optionally followed by centrifugation of the sample.

In some embodiments, following a sample preparation step (e.g., purification, extraction), the sample is dissolved in a diluent containing at least about 60% organic solvent or at least about 70% organic solvent, or at least about 80% organic solvent, or at least about 90% organic solvent. In other embodiments, following a sample preparation step, the sample includes a polar or non-polar organic solvent or a mixture of organic solvents, or a mixture of water or an aqueous solution and a water-miscible polar organic solvent, e.g., methanol, ethanol, isopropanol, tetrahydrofuran, dichlormethane, hexane, N,N-dimethylformamide, dimethylsulfoxide, acetonitrile or a combination thereof. In an embodiment, the sample aqueous solution is an acidic, basic or neutral solution having between about 1% and about 99% water by volume. The sample solution comprising the analyte can, optionally, further contain one or more additional analytes. In one embodiment, the sample solution is an aqueous solution which includes a complex variety of analytes.

In one embodiment, the extracted or purified sample which may include an aqueous or organic solvent or diluent is dried and subsequently reconstituted in a solvent (e.g., water or water/organic mixture) that is compatible with the mobile phase of the method and system of the subject technology. This is known as a solvent exchange step. For example, the extracted or purified sample is dried and then reconstituted in methanol or in methanol and water.

In another embodiment, the extracted or purified sample which is dissolved in an aqueous or organic solvent or in a diluent with at least 60% organic solvent will not undergo solvent exchange or will not be subject to a solvent exchange step before being analyzed by the method and/or system of the subject technology. The absence of a solvent exchange step shortens the analysis period and improves the run time of the method of subject technology.

In some embodiments, sample is prepared with or extracted in an organic solvent wherein the prepared sample is analyzed by the method of the subject technology without additional sample derivatization or solvent exchange step (i.e., drying of the solvent and reconstituting the analytes or solutes with a different solvent). The absence of a derivatization step shortens the analysis period and improves the run time of the method of subject technology.

In certain embodiments, the analytes are derivatized before analysis by the method and/or system of the subject technology. Various methods for derivatizing steroids and steroid derivatives are known in the art. In general derivatization fall into three general reaction types: (1) Alkylation of which the general process is esterification, (2) Acylation and (3) Silylation. Common derivatization reagents for the Alkylation type of reactions are Dialkylacetals, Diazoalkales, Pentafluorobenzyl bromide (PFBBr), Benzylbromide, Boron trifluoride (BF3) in methanol or butanol and Tetrabutylammonium hydroxide (TBH) among others. Reagents used for the silylation derivatization process include Hexamethyldisilzane (HMDS), Trimethylchlorosilane (TMCS), Trimethylsilylimidazole (TMSI), Bistrimethylsilylacetamide (BSA), Bistrimethylsilyltrifluoroacetamide (BSTFA), N-methyltrimethylsilyltrifluoroacetamide (MSTFA), Trimethylsilyldiethylamine (TMS-DEA), Nmethyl-N-t-butyldimethylsilyltrifluoroacetamide (MTBSTFA), and Halomethylsilyl derivatization reagents. Common reagents for the Alkylation process are Fluoracylimidazoles, Fluorinated Anhydrides, N-Methyl-bis(trifluoroacetamide) (MBTFA), Pentafluorobenzoyl Chloride (PFBCl) and Pentafluoropropanol (PFPOH).

In certain embodiments, an internal standard can be added to a sample prior to sample preparation. Internal standards can be useful to monitor extraction/purification efficiency. An internal standard can be added to a sample and allowed to equilibrate for a period of time, e.g., 5, 10, 15, 20, 25, 30, 60, 120 or more minutes. Equilibration temperature can be from about 10° C. to about 45° C., or any value in between (e.g., 15, 25, 30, 35, 37, 42, or 44° C.). In certain cases, equilibration can be at room temperature for about 15 minutes.

An internal standard can be any compound that would be expected to behave under the sample preparation conditions in a manner similar to that of one or more of the analytes of interest. For example, a stable-isotope-labeled version of an analyte of interest can be used, such as a deuterated version of an analyte of interest. While not being bound by any theory, the physicochemical behavior of such stable-isotope-labeled compounds with respect to sample preparation and signal generation would be expected to be identical to that of the unlabeled analyte, but clearly differentiable by mass on a mass spectrometer.

To improve the run time and minimize hands-on sample preparation, on-line extraction and/or analytical chromatography of a sample can be used. For example, in certain methods, a sample, such as a deproteinized plasma sample, can be extracted using an extraction column, followed by elution onto an analytical chromatography column. The columns can be useful to remove interfering components as well as reagents used in earlier sample preparation steps (e.g., to remove reagents such as acetonitrile). Systems can be coordinated to allow the extraction column to be running while an analytical column is being flushed and/or equilibrated with solvent mobile phase, and vice-versa, thus improving efficiency and run-time. A variety of extraction and analytical columns with appropriate solvent mobile phases and gradients can be chosen by those having ordinary skill in the art.

Various extraction methods are known in the art that can be used to prepare a sample before it being analyzed by the method and system of the subject technology. Such extraction methods include, but are not limited to, sonication, soxhlet extraction, microwave assisted extraction (MAE), supercritical fluid extraction (SFE), accelerated solvent extraction (ASE), pressurized liquid extraction (PLE), pressurized hot water extraction (PHWE) and/or surfactant assisted extraction (PHWE) in common solvents such as methanol, ethanol, mixtures of alcohols and water, or organic solvents such as ethyl acetate or hexane.

In some embodiments, the concentration of the steroids or steroid derivatives (i.e., analytes) in the sample solution being analyzed by the method and system of the subject technology is about 1 mg/mL, 0.5 mg/mL, 0.1 mg/mL, 0.05 mg/mL, 0.01 mg/mL, 0.005 mg/mL, 0.001 mg/mL, 0.0001 mg/mL, $1\times10^{-5}$ mg/mL, $1\times10^{-6}$ mg/mL or less. In an embodiment, the concentration of the steroids or steroid derivatives (i.e., analytes) in the sample solution being analyzed by the method and system of the subject technology is in ng/mL or pg/mL range. In another embodiment, the sample injection volume for injection into the $CO_2$ based system or the chromatography column of the subject technology is about 10 µL, 8 µL, 6 µL, 5 µL, 4 µL, 3 µL, 2 µL, 1 µL.

Detection

In some embodiments, suitable detection methods for detecting the analytes (i.e., steroids or steroid derivatives) include, but not limited to, UV, photodiode array (PDA), Evaporative Light Scattering (ELS), CD, FID, and Mass Spectrometry (MS).

Depending on the sample that is being analyzed by the method and system of the subject technology, a suitable detector may be used. Suitable detectors are known in the art. For example, if the sample is pharmaceutical formulation and the source of analytes is active pharmaceutical ingredients (API), due to the abundance of the sample or analytes (i.e., about 1-10 ppm range or 1 to 10 µg/mL), a detection method such as UV, PDA or ELS may be used. If the sample is of biological origin, e.g., plasma, blood, saliva, urine, spinal fluid (in which the analyte concentration is in ng/mL or pg/mL range), a detection method such as Mass Spectrometry may be used.

Kits

One embodiment of the subject technology features a kit for performing the method of the subject technology. As used herein, the term kit refers to a collection of parts and reagents bundled together with suitable packaging and instructions for their use. One kit for performing an analysis of a sample for the analytical levels or the presence or absence of steroids or steroid derivatives, in accordance with the subject technology includes: internal standards for calibrating and facilitating the identification of one or more steroids; calibrators; controls; tuning mixtures; sample preparation devices or reagents and materials for forming sample purification, extraction, preparation or derivatization; and a chromatography column for separating or detecting the steroids and steroid derivatives of the sample.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented. Furthermore, to the extent that the term "include," "have," or the like is used in the description or the claims, such term is intended to be inclusive in a manner similar to the term "comprise" as "comprise" is interpreted when employed as a transitional word in a claim.

This subject technology is further illustrated by the following examples which should not be construed as limiting. The contents of all references, patents and published patent applications cited throughout this application, are incorporated herein by reference.

EXAMPLES

Example 1

Rapid Analysis of Natural Steroids

A sample of nine closely related natural steroids (i.e., androstenedione; 17α-hydroxyprogesterone; testosterone; estrone; 11-deoxycortisol; corticosterone; aldosterone; cortisol; estradiol) was prepared and injected to the $CO_2$-based system of the subject technology. Preliminary data obtained using a BEH 2-EP column (1.7 µm, 3.0 mm×50 mm) column with UV detection demonstrates excellent resolution of 9 critical steroids in approximately two minutes (FIG. 4).

These results demonstrated that the $CO_2$-based system and/or method of the subject technology provides a rapid analytical method for detecting steroids and steroid derivatives.

Example 2

Rapid Analysis of Synthetic Steroids

In this example, the $CO_2$-based system and method of the subject technology were tested for analysis of synthetic steroids and steroid derivatives. Using a BEH 2-EP column (1.7 µm, 3.0 mm×50 mm) in the $CO_2$-based system of the subject technology, a mixture of 6 structurally similar synthetic steroids was eluted in approximately 2 minutes (FIG. 5). In the current example, the co-elution of peaks 5 and 6 under UV detection, would be resolved under mass spectroscopy (MS) conditions, with compound molecular weights of 360.44 g/mole (prednisolone) and 392.46 g/mole (betamethasone).

These results demonstrated that the $CO_2$-based system and/or method of the subject technology provides a rapid analytical method for detecting steroids. This example also showed that optimization and the use of other column geometries or application of other detection methods such as MS in place of UV detection further enhances the analyses of the closely related steroids.

Example 3

Separation and Analysis of Sulfated Estrogens

In this example, the $CO_2$-based system and method of the subject technology was used for separation and analysis of sulfated estrogens. The chromatographic analysis of steroids and steroid derivatives often presents a difficult challenge due to their structural similarities. Even with the inclusion of mass spectrometric detection, due to the isobaric nature of many of these compounds, chromatographic resolution is often required. One such group of compounds is the conjugated estrogens. Because free steroids have limited aqueous solubility, they are often found biologically in a conjugated form, which for mammals can be as sulfates or glucuronates. The resulting ester formed with the negatively charged hydrophilic side groups increase their aqueous solubility, and thus their bioavailability. The sulfated estrogens are frequently used as hormone replacement therapy for post-menopausal women, both to provide symptomatic relief from vasomotor symptoms (hot flashes) and for the prevention of osteoporosis. They have also been used in the treatment of hormone deficiencies in younger women. Because of these treatment regimes, there is great interest in the development and characterization of therapeutic preparations of the sulfated estrogens. Typical methods employing gas chromatography (GC) involve lengthy sample preparation and derivatization steps, and results in inadequate resolution for one isobaric pair of compounds. Additional methods have been developed utilizing LC/MS yielding a relatively complex method requiring approximately 90 minutes for analysis.

Figure 6:
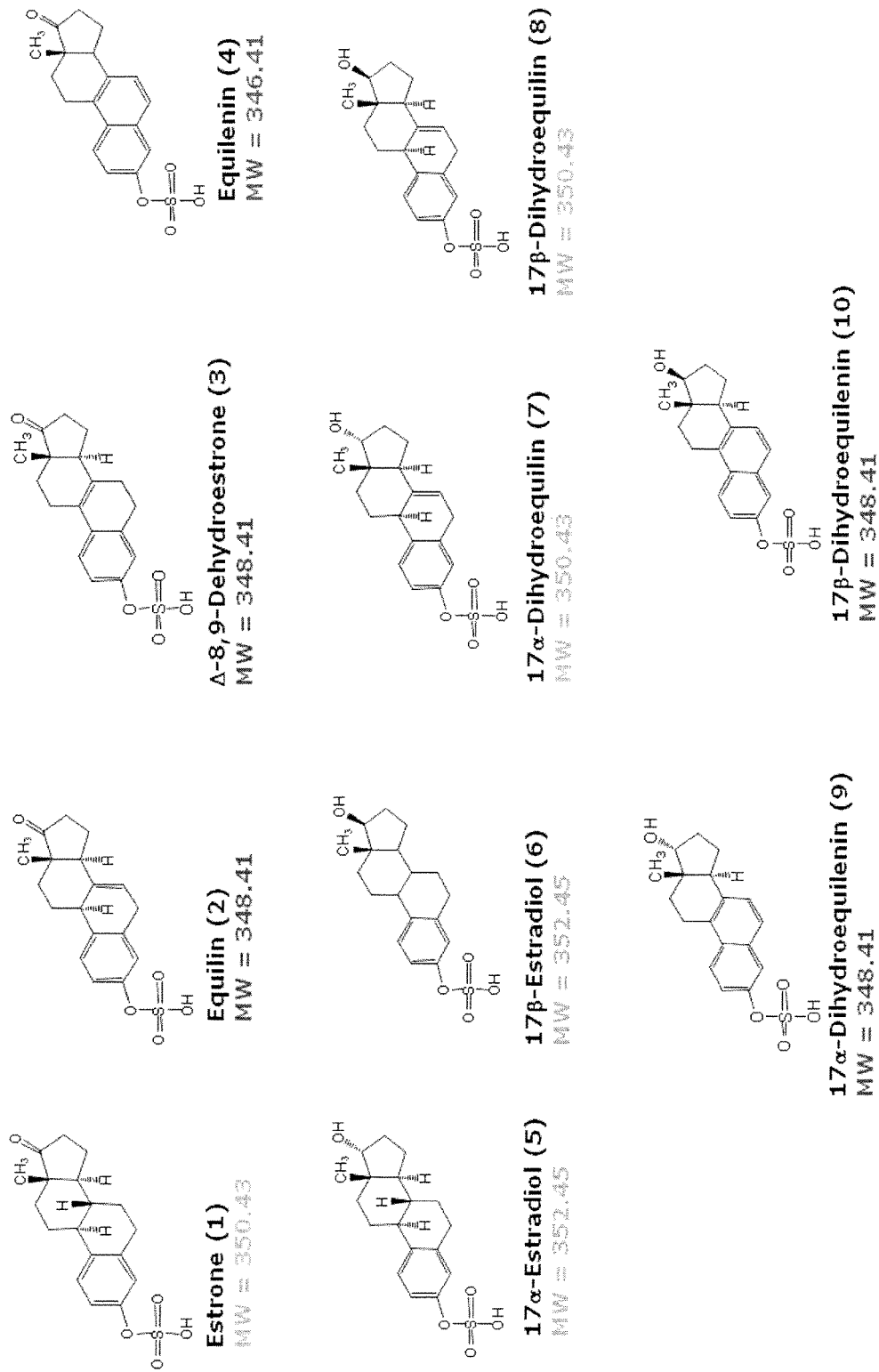
FIG. 6 shows the chemical structures of ten sulfated estrogens studied in Example 3.

In this example, the separation of 10 structurally similar sulfated estrogens (FIG. 6) is shown using the method and system of the subject technology. As seen in FIG. 6, some of the compounds have identical molecular weight, which indicates that they are isobaric.

Experimental:

Sample Preparation

Stock solutions were prepared from individual sulfated estrogen samples using methanol (MeOH), ethanol (EtOH), and 2-propanol (IPA) as diluents. The stock solutions were used to prepare the final sample mixture, at the concentrations shown in Table 1, using ethanol as a diluent.

TABLE 1

Stock and Sample Preparation

| Peak # | Sulfated Estrogens | Molecular Weight | Stocks Conc. (mg/mL) | Diluent | Sample Mix (in EtOH) Final Conc. (mg/mL) |
|---|---|---|---|---|---|
| 1 | Estrone | 350.43 | 3 | 30:70 IPA/EtOH | 0.4 |
| 2 | Equilin | 348.41 | 5 | EtOH | 0.4 |
| 3 | Δ-8,9-Dehydroestrone | 348.41 | 3 | EtOH | 0.4 |
| 4 | Equilenin | 346.41 | 3 | 40:60 MeOH/EtOH | 0.05 |
| 5 | 17α-Estradiol | 352.45 | 10 | EtOH | 0.4 |
| 6 | 17β-Estradiol | 352.45 | 10 | EtOH | 0.4 |
| 7 | 17α-Dihydroequilin | 350.43 | 5 | EtOH | 0.4 |
| 8 | 17β-Dihydroequilin | 350.43 | 10 | EtOH | 0.4 |
| 9 | 17α-Dihydroequilenin | 348.41 | 10 | EtOH | 0.05 |
| 10 | 17β-Dihydroequilenin | 348.41 | 10 | EtOH | 0.05 |

Method Conditions:

Parameters: System: The $CO_2$ based system of the subject technology with a PDA detector; Chromatography Column: Solid stationary phase hybrid particles with 2-Ethylpyridine surface modification, mean particle size: 1.7 μm, 3.0 mm (internal diameter), 100 mm (column length); Mobile Phase A: $CO_2$ (tank, medical grade); Mobile Phase B (modifier): Methanol with additional additives, as specified for each chromatogram; Column Temp.: 20-50° C.; Automatic Back Pressure Regulator (ABPR): 1700-4100 psi; UV Detection: 220 nm (Compensated 380-480 nm) [40 pts/sec]; Injection Volume: 1.5 μL; Strong Needle Wash: Methanol; Weak Needle Wash: 2-Propanol (IPA); Seal Wash: Methanol; Gradient Conditions: As shown with individual chromatograms; Vials: LCMS Certified Max Recovery Vials.

Figure 7:
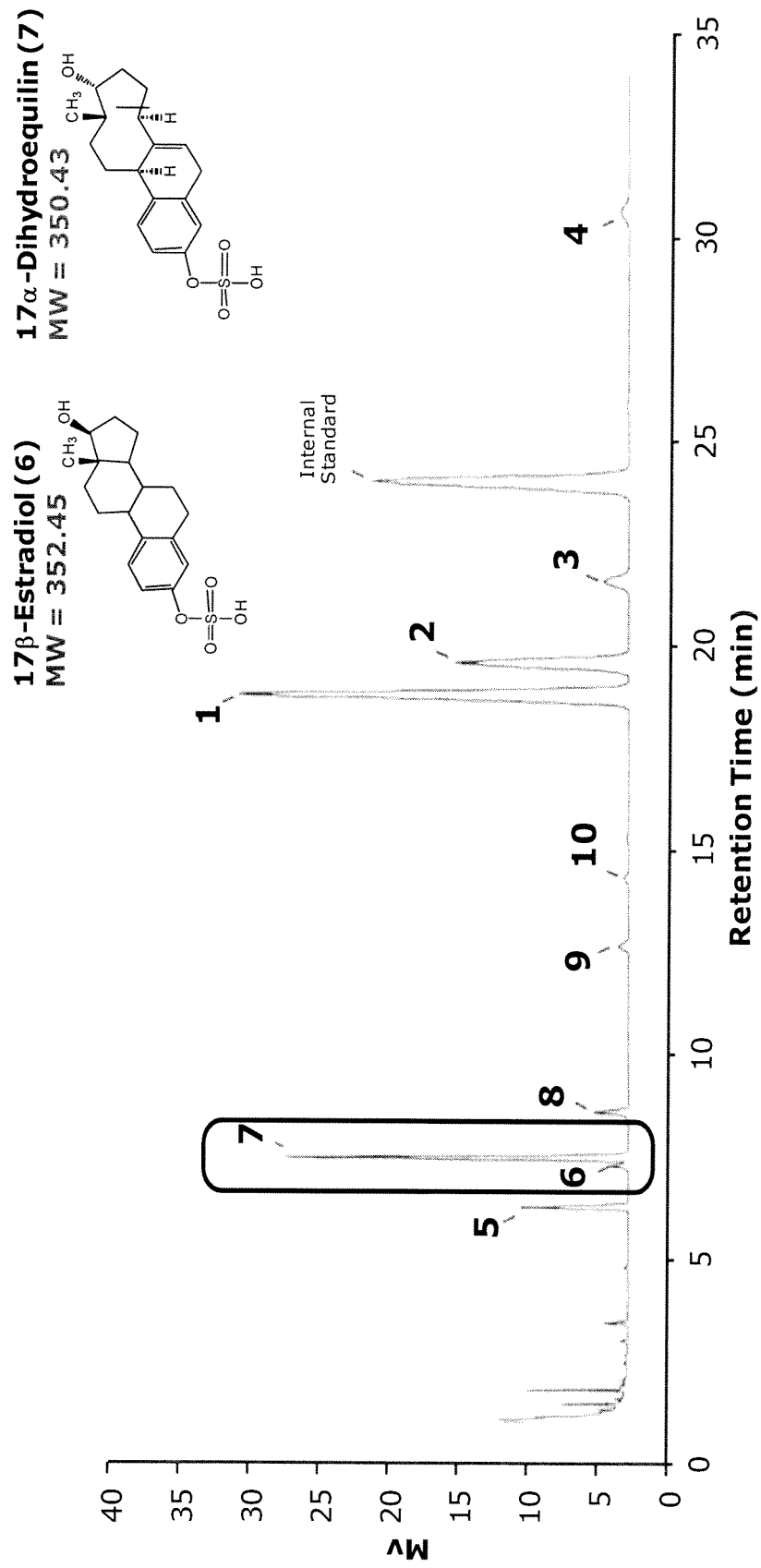
FIG. 7 is an exemplary illustration showing the separation of ten sulfated estrogens depicted in FIG. 6 using gas chromatography. The isobaric compounds (compounds with similar molecular weights, peaks 5 and 6) have been circled in the figure.

Results and Discussion:

The current USP method for the characterization of conjugated estrogens utilizes GC analysis of the derivatized estrogens. Prior to the derivatization of the estrogens, the conjugated estrogen must be treated to cleave the sulfate group using a sulfatase enzyme. This process takes approximately two hours with multiple steps involving shaking, sonication, water baths, centrifuging, buffers, pH adjustments, and filtration. The derivatization step requires another 25 minutes with the addition of pyridine, bis(trimethylsilyl)trifluoroacetamide and trimethylchlorosilane. The sample is then analyzed by a 35-minute GC-FID method. As can be seen from FIG. 2, even under these conditions, with a total sample preparation and analysis time of about 3 hours, the isobaric 17α- and 17β-estradiols (MW=352.45) are not completely resolved. See FIG. 7.

In accordance with an implementation of the method and the $CO_2$ based system of the subject technology, without the need for sulfate removal followed by derivatization, preparation of the sample for analysis is significantly faster and easier than for GC analysis, and involves simple dilution of the sulfated estrogens in the appropriate diluents (see Table 1). For this exemplary application, the goal was to test various conditions and parameters to separate the 10 sulfated estrogens with resolution values (RS) greater than 1.5, with UV detection.

(I) Different Combinations of Stationary Phase and Mobile Phase Modifier

Figure 8:
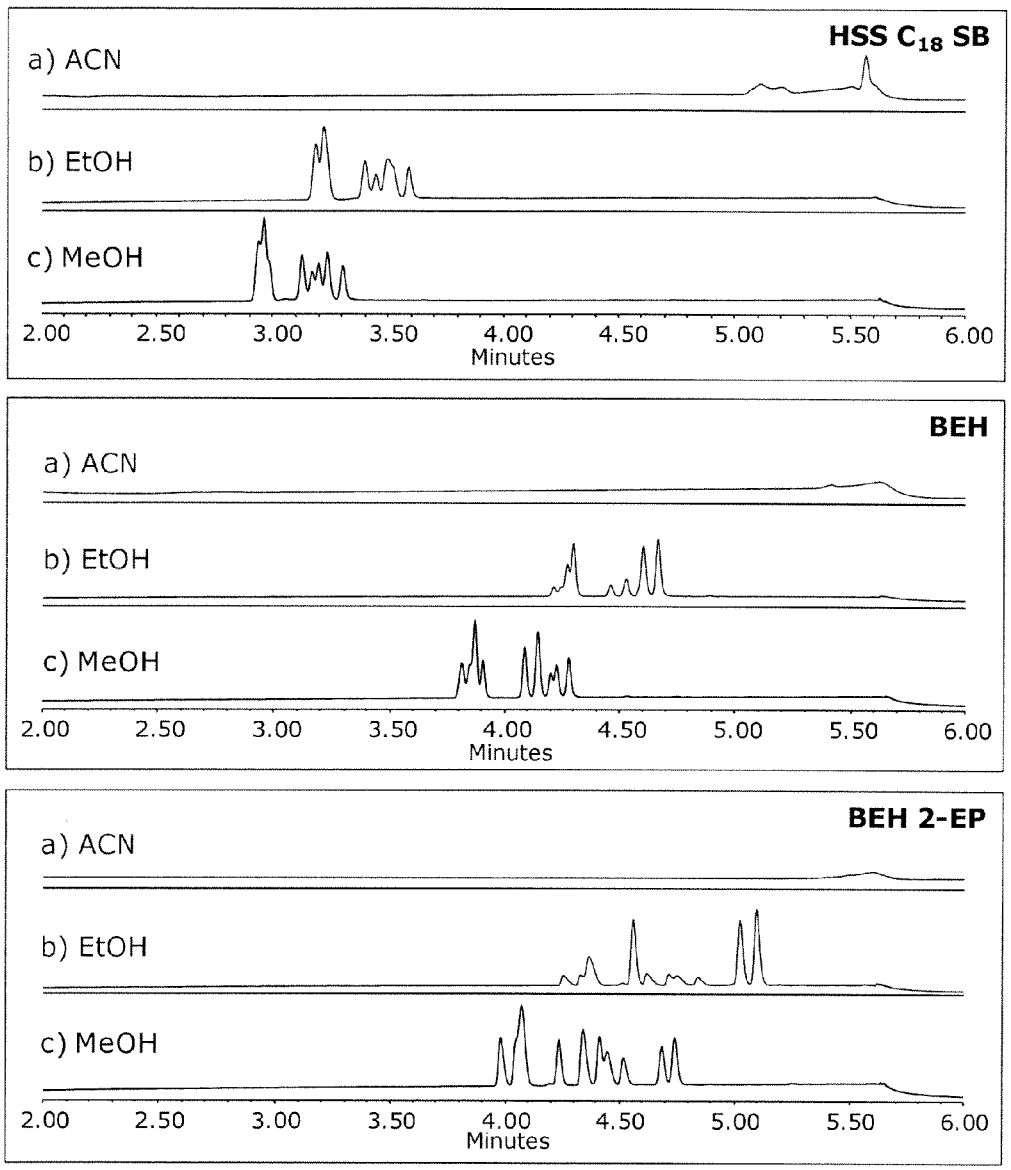
FIG. 8 is an exemplary illustration showing the column chromatography analysis of the sulfated estrogen mixture using different stationary and mobile phase chemistries. For all of the chromatograms shown, the physical dimensions of the chromatography columns were 3.0 mm (ID)×100 mm (length), all by Waters Corp, Milford, Mass. The stationary phases were as follow: (top): silica particles with polar/non-polar surface moieties (i.e., HSS $C_{18}$ SB particles with $C_{18}$ surface modifications and no endcapping of the surface silanol groups) and with a mean diameter of 1.8 μm, (middle): hybrid particles with polar surface moieties (i.e., BEH particles with free surface silanol groups) with a mean diameter of 1.7 μm, and (bottom): hybrid particles with polar surface moieties (i.e., BEH 2-Ethylpyridine particles with 2-ethylpyridine surface modifications and no endcapping of the surface silanol groups) and with a mean diameter of 1.7 μm. ACN (a), EtOH (b), and MeOH (c) were used as mobile phase modifiers. In each case, 10 mM ammonium acetate (AmOAc) and 5% water were added to the modifier. A 5-minute gradient of 5-50% modifier was run with a flow rate of 1.3 mL/min at 50° C. The ABPR settings were 1600 psi for the HSS C18 SB column and 2175 psi for the BEH and BEH 2-EP columns.

Preliminary method screening was performed using different combinations of stationary phase and mobile phase modifier with the addition of a modifier additive. Additives have been shown to play a critical role in the retention mechanisms governing separations with liquid CO2, with several hypotheses as to their function: suppression of ionization, formation of ion pairs, coverage of stationary phase active sites, or altering the polarity of the stationary and/or mobile phases. For the current example, without the addition of basic, acidic or salt additives to the mobile phase modifier, the charged estrogen sulfates are not eluted from the column (data not shown). Initial evaluations utilized 10 mM ammonium acetate (AmOAc) with 5% water as additives in methanol (MeOH), ethanol (EtOH), or acetonitrile (ACN). The results from this screening using three different chromatography columns, i.e., hybrid particles with no surface modification (e.g., BEH particles), hybrid particles with polar surface modification (e.g., BEH 2-Ethylpyridine), and silica particles with polar/non-polar surface modification (e.g., HSS C18 SB, in which unbounded silanol groups are uncapped) are shown in FIG. 8.

(II) Effect of Additives to the Modifier

Figure 9:
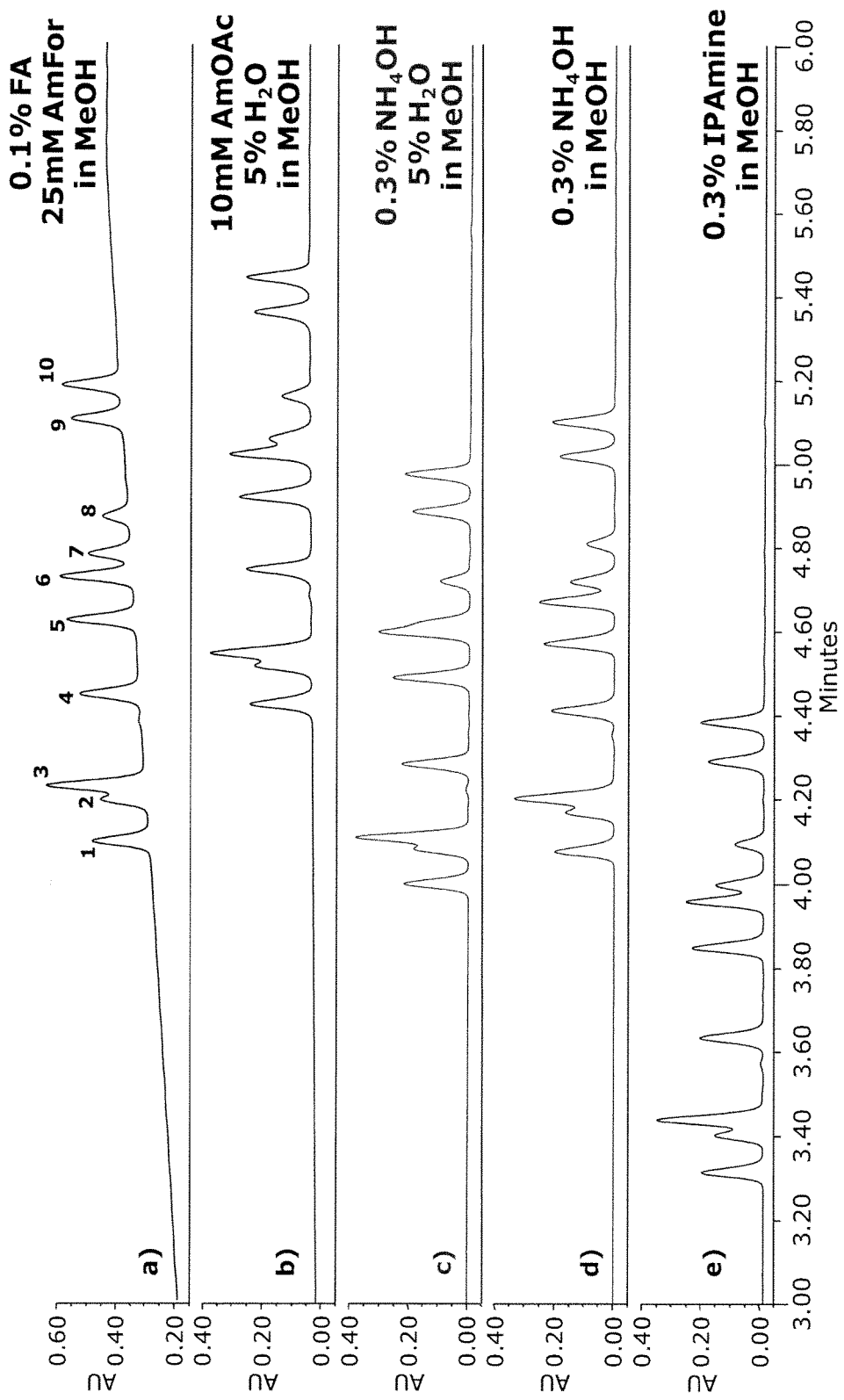
FIG. 9 is an exemplary illustration showing the screening of the estrogen mixture using a chromatography column packed with hybrid particles with a polar surface functionality (i.e., a BEH 2-EP, 1.7 μm, 3.0×100 mm column, Waters Corp., Milford, Mass.) and a methanol modifier including additives as follows: (a) 0.1% formic acid and 25 mM ammonium formate; (b) 10 mM ammonium acetate and 5% water; (c) 0.3% ammonium hydroxide and 5% water; (d) 0.3% ammonium hydroxide; (e) and 0.3% isopropyl amine. For each experiment, a 5-minute gradient from 9-40% modifier was run with a flow rate of 1.3 mL/min at 50° C. The Automated Back Pressure Regulator (ABPR) setting was 2175 psi. For peak identities in panel (a), and the corresponding peaks in panels (b)-(e), see Table 1.

As seen in section (I), the use of a modifier additive was necessary for the charged analytes to elute from the chromatography column. Using ammonium acetate in water as the additive, the optimum separation was obtained on the BEH 2-EP column with methanol as the modifier. The choice of additive can have significant impact on the retention and resolution, so various additives were next explored. Due to the analyte retention window observed for the column screening example, the gradient slope for these evaluations was decreased by using a smaller range of modifier concentration, with a gradient from 9% to 40% modifier. All other parameters remained the same. FIG. 9 shows the impact of the various additives on the separation.

In each of the examples with the various additives, the elution order remains the same. Only the retention times and resolution is impacted by the choice of additive. As can be seen from the separations in FIG. 9, there are two sets of critical pairs for resolution; peaks 2 and 3, and peaks 6 and 7. Based on the resolution for these two pairs, there are multiple additives that may be acceptable with further optimization. The choice for which set of conditions to move forward with may depend on the ultimate goals of the separation. If this final method was intended for mass spectrometric detection, optimization may focus on either the ammonium hydroxide or the formic acid/ammonium formate additives due to their compatibility with the detection technique. For the current evaluation, using UV detection, the isopropyl amine (IPAmine) additive was selected for further optimization.

(III) Pressure Effects

It is well known that separations using liquid $CO_2$ as a mobile phase have analyte retention factors that are greatly influenced by the density of the mobile phase. Because of the compressibility of liquid $CO_2$, the density can change significantly with changes in pressure, resulting in retention factors decreasing with increasing mobile phase density (pressure). In addition, the selectivity and resolution of individual analytes may be impacted as they respond differently to the changes in mobile phase density. Using isopropyl amine as the additive, the effects of pressure were studied by varying the pressure setting for the Automated Back Pressure Regulator (ABPR) on the $CO_2$ based system of the subject technology, with pressures from 1700 psi to 3200 psi. The results are shown in FIG. 10.

Figure 10:
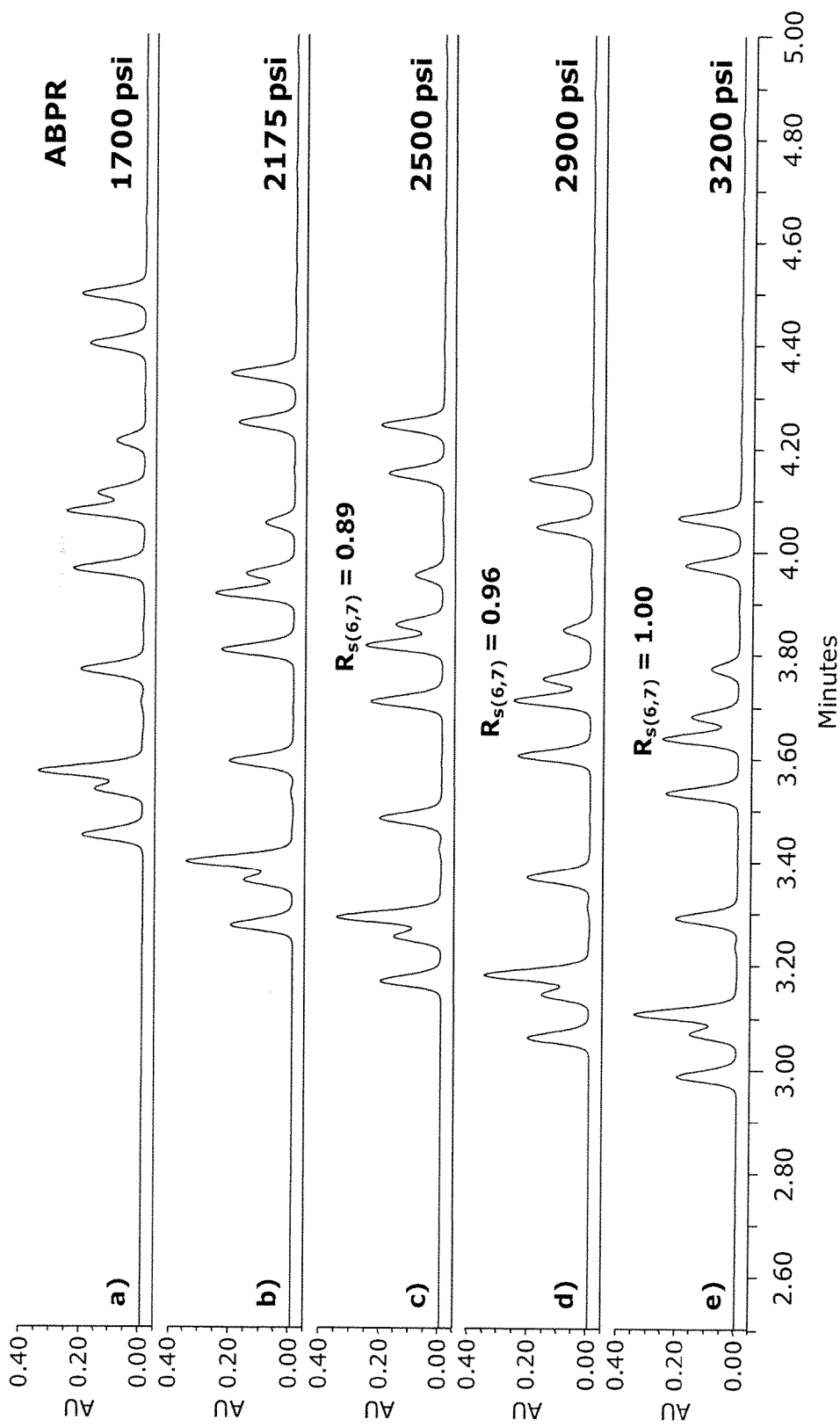
FIG. 10 is an exemplary illustration showing the screening of the estrogen mixture using a chromatography column packed with hybrid particles with a polar surface functionality (i.e., a BEH 2-EP, 1.7 μm, 3.0×100 mm column, Waters Corp., Milford, Mass.) with methanol as the modifier and 0.3% isopropyl amine as the additive. The ABPR settings were as follow: 1700 psi (a), 2175 psi (b), 2500 psi (c), 2900 psi (d), and 3200 psi (e). A 5-minute modifier gradient from 9-40% was run with a flow rate of 1.3 mL/min at 50° C. The peak identities in this figure correspond to those shown in FIG. 9, panel (a).

With attention to the two critical pairs, FIG. 10 shows that for this set of analytes, the resolution of peaks 2 and 3 is not significantly impacted by changes in pressure, while for peaks 6 and 7, the resolution is improved slightly at the higher pressure, higher density conditions. The greatest resolution for peaks 6 and 7 ($RS(6,7)=1.00$) was observed with an ABPR setting of 3200 psi.

(IV) Temperature Effects

Figure 11:
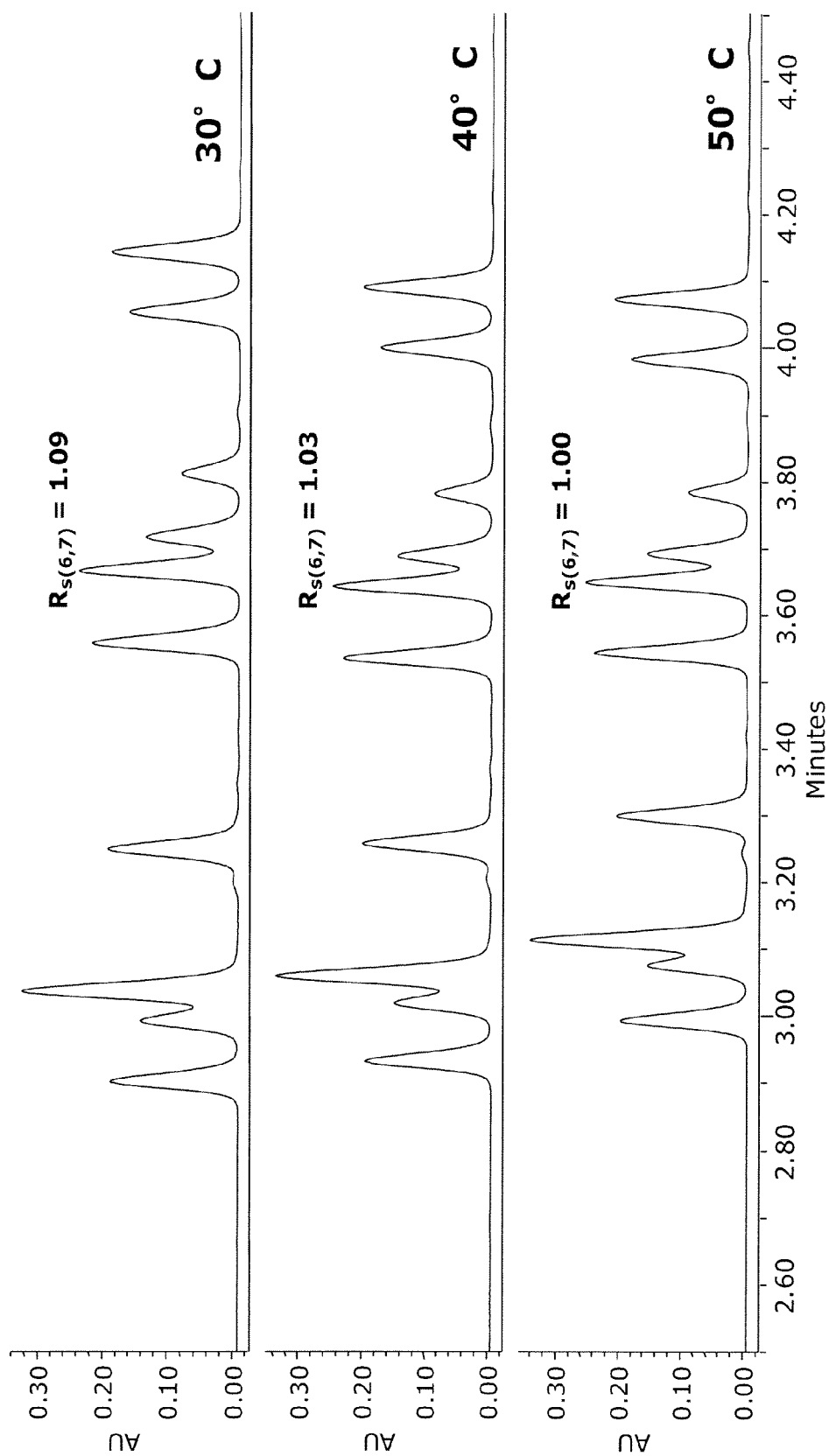
FIG. 11 is an exemplary illustration showing the screening of the estrogen mixture using a chromatography column packed with hybrid particles with a polar surface functionality (i.e., a BEH 2-EP, 1.7 μm, 3.0×100 mm column; Waters Corp. Milford, Mass.) with methanol as the modifier and 0.3% isopropyl amine as the additive at various temperatures: 30° C. (top), 40° C. (middle), and 50° C. (bottom). A 5-minute modifier gradient from 9-40% was run with a flow rate of 1.3 mL/min and with an ABPR setting of 3200 psi. The peak identities in this figure correspond to those shown in FIG. 9, panel (a).

Temperature can also be useful a tool to influence selectivity and resolution. Using the highest ABPR setting of 3200 psi, further evaluations were performed at 40 and 30° C., as shown in FIG. 11.

Again, focusing on the critical pairs, it can be seen that the decrease in temperature results in the increase in resolution for both critical pairs. The optimum separation for these analytes is achieved at the lowest temperature evaluated, 30° C.

(V) Flow Rate Effects

Figure 12:
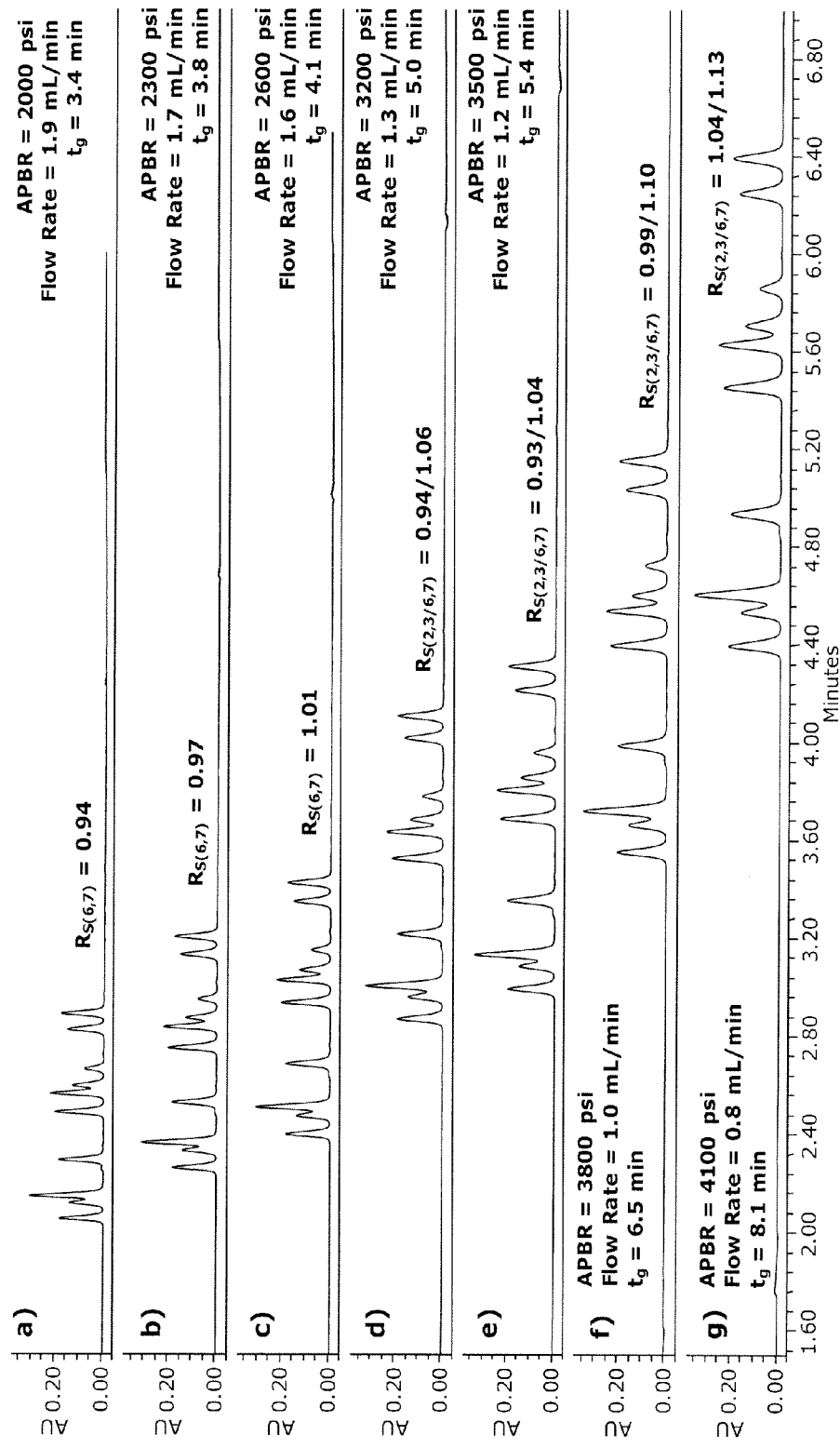
FIG. 12 is an exemplary illustration showing the screening of the estrogen mixture using a chromatography column packed with hybrid particles with a polar surface functionality (i.e., a BEH 2-EP, 1.7 μm, 3.0×100 mm column; Waters Corp. Milford, Mass.) with methanol as the modifier and 0.3% isopropyl amine as the additive, with variable ABPR settings. At each pressure setting, the flow rate was adjusted to the fastest flow possible within the pressure specifications of the $CO_2$ based system of the subject technology. In addition, the gradient time ($t_g$) was adjusted for each flow rate to maintain the same gradient volume (13.9 column volumes) for each separation. The settings for ABPR, flow rate, and $t_g$ were as follow: 2000 psi, 1.9 mL/min, 3.4 min (a), 2300 psi, 1.7 mL/min, 3.8 min (b), 2600 psi, 1.6 mL/min, 4.1 min (c), 3200 psi, 1.3 mL/min, 5.0 min (d), 3500 psi, 1.2 mL/min, 5.4 min (e), 3800 psi, 1.0 mL/min, 6.5 min (f), and 4100 psi, 0.8 mL/min, 8.1 min (g). The gradient was 9-40% modifier at 30° C. The peak identities in this figure correspond to those shown in FIG. 9, panel (a).

Because of the codependent relationship between flow rate and pressure, exploring the effects of flow rate requires pressure to be considered as a parameter. In the earlier evaluation of pressure effects, the best separations were achieved at the higher pressures. Because of this, as the various flow rates were explored, the ABPR pressure setting was adjusted to maintain the highest possible pressures during the separation within the specifications of the $CO_2$ based system. In addition, the gradient times ($t_g$) were adjusted based on the flow rate used so that the number of column volumes was the same for each separation (13.9 column volumes), thus the $t_g$ was increased for the lower flow rates, while the tg was decreased for the faster flow rates. The separations at flow rates from 0.8 mL/min to 1.9 mL/min are shown in FIG. 12.

For each set of conditions, the resolution values for the critical pairs were recorded when possible, as shown in Table 2. The highest resolution for both pairs was obtained at the lowest flow rate evaluated (0.8 mL/min), using an ABPR setting of 4100 psi and a gradient time of 8.1 minutes.

TABLE 2

Resolution of critical peak pairs as a function of flow rate

| ABPR (psi) | Flow Rate (mL/min) | Maximum System Pressure (psi) | $t_g$ (min) | $R_{S(2,3)}$ | $R_{S(6,7)}$ |
|---|---|---|---|---|---|
| 2000 | 1.9 | 5723 | 3.4 | — | 0.94 |
| 2300 | 1.7 | 5638 | 3.8 | — | 0.97 |
| 2600 | 1.6 | 5751 | 4.1 | — | 1.01 |
| 3200 | 1.3 | 5791 | 5.0 | 0.94 | 1.06 |
| 3500 | 1.2 | 5915 | 5.4 | 0.93 | 1.04 |
| 3800 | 1.0 | 5806 | 6.5 | 0.99 | 1.10 |
| 4100 | 0.8 | 5716 | 8.1 | 1.04 | 1.13 |

(VI) Flow Gradients

Figure 13:
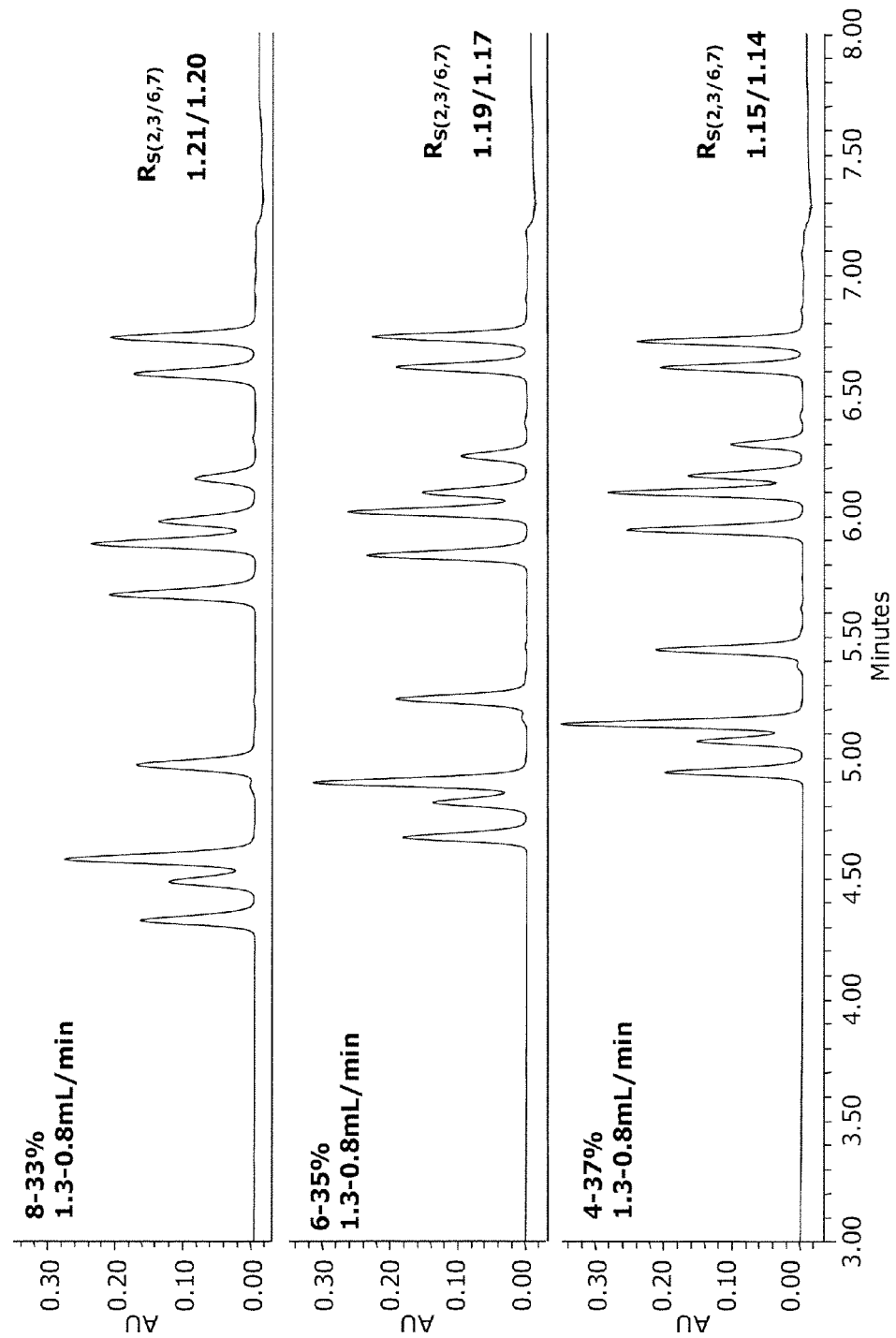
FIG. 13 is an exemplary illustration showing the separation of the estrogen mixture using a chromatography column packed with hybrid particles with a polar surface functionality (i.e., a BEH 2-EP, 1.7 μm, 3.0×100 mm column; Waters Corp., Milford, Mass.) with methanol as the modifier and 0.3% isopropyl amine as the additive, employing a flow gradient from 1.3 to 0.8 mL/min. For each example, the gradient slope was adjusted by changing the beginning and ending modifier concentrations: 8-33% (top), 6-35% (middle), and 4-37% (bottom). For each experiment, the gradient time ($t_g$) was 6.2 minutes at 30° C. with an ABPR setting of 4100 psi. The peak identities in this figure correspond to those shown in FIG. 9, panel (a).

Throughout the preliminary screening of these compounds under a variety of conditions, including various pressure and flow rate settings, it was consistently observed that the best separations were obtained at conditions with the highest pressures. However, as the gradient transitions to higher modifier concentrations, the increased mobile phase viscosity results in higher system pressures, leading to system over-pressure shut down above 6000 psi. In order to stay within the pressure specifications of the system, flow rates lower than the optimum linear velocity are required, resulting in a lower efficiency separation with lower peak capacities. To achieve the fastest separations with the greatest peak capacity, reverse flow-gradients can be used to maintain the system pressure at a nearly constant level near the upper specification for the system. As the percent concentration of organic modifier is increased, the flow rate is decreased. This can be seen in the gradient table shown in FIG. 13 for the separation of the sulfated estrogens using methanol as the modifier with 0.3% isopropyl amine (IPAm) as the additive. As the percent modifier transitions from 9% to 40%, the flow rate is decreased from 1.3 mL/min to 0.8 mL/min, the maximum flow rates that were determined empirically at each concentration of mobile phase modifier.

Figure 14:
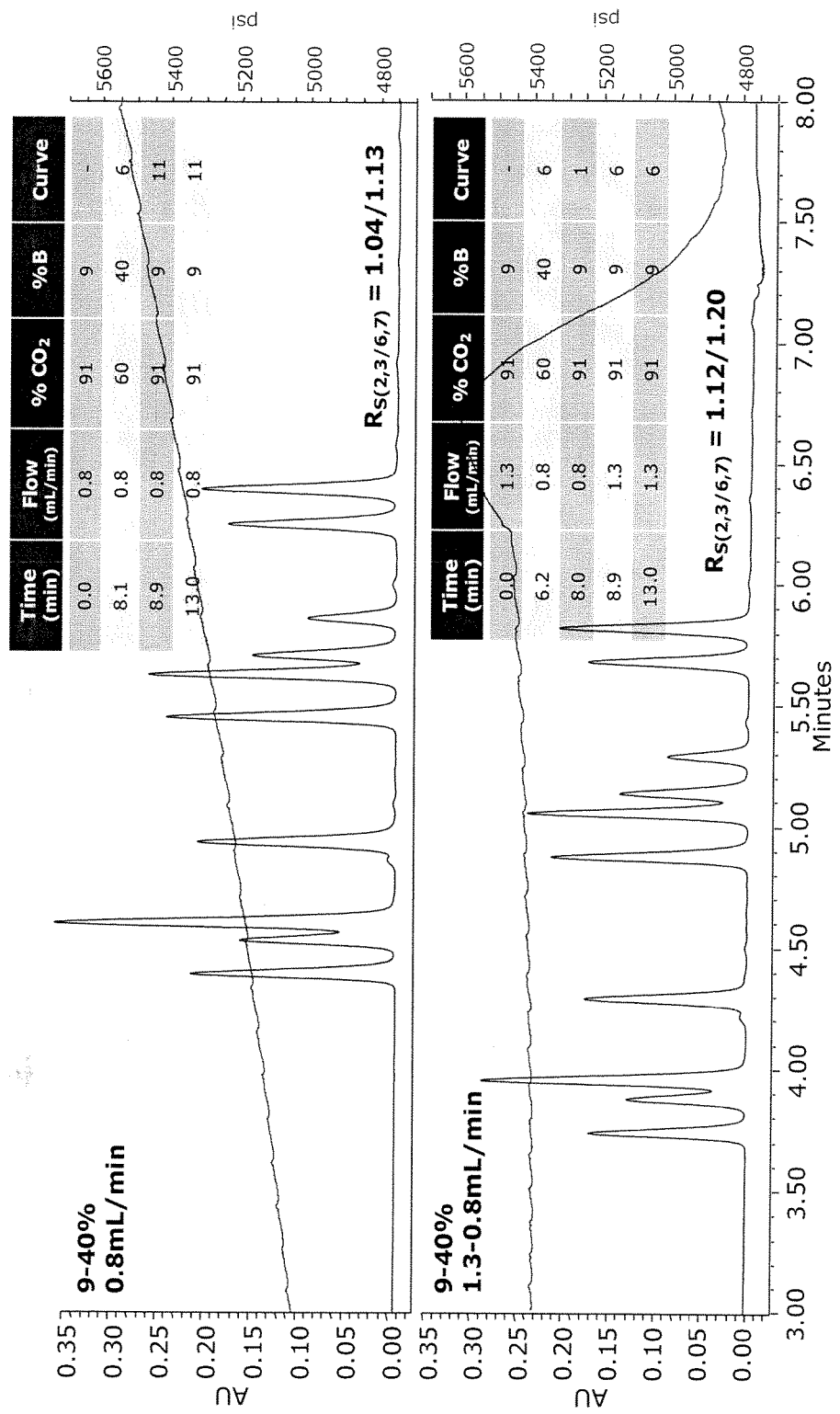
FIG. 14 is an exemplary illustration showing the separation of the estrogen mixture using a chromatography column packed with hybrid particles with a polar surface functionality (i.e., a BEH 2-EP, 1.7 μm, 3.0×100 mm column; Waters Corp., Milford, Mass.) with methanol as the modifier and 0.3% isopropyl amine as the additive, with a constant flow rate of 0.8 mL/min (top), and employing a flow gradient from 1.3 to 0.8 mL/min (bottom). For the flow gradient, the gradient time ($t_g$) was adjusted to maintain the same gradient volume (13.9 column volumes) as in the constant flow example. For both experiments, the gradient was 9-40% modifier at 30° C. with an ABPR setting of 4100 psi. The gradient tables along with the system pressure traces for each separation are shown in the figure. The peak identities in this figure correspond to those shown in FIG. 9, panel (a).

FIG. 14 compares the separation at constant flow with that using a flow gradient, with the resulting system pressure traces shown by the line that goes across each chromatogram. For the flow gradient, the system pressure is nearly constant throughout the gradient retention window. The use of the flow gradient enables collection of data at flow rates as close to the optimum linear velocity as possible, within the pressure specifications of the system, maximizing the overall peak capacity of the separation.

Figure 15:
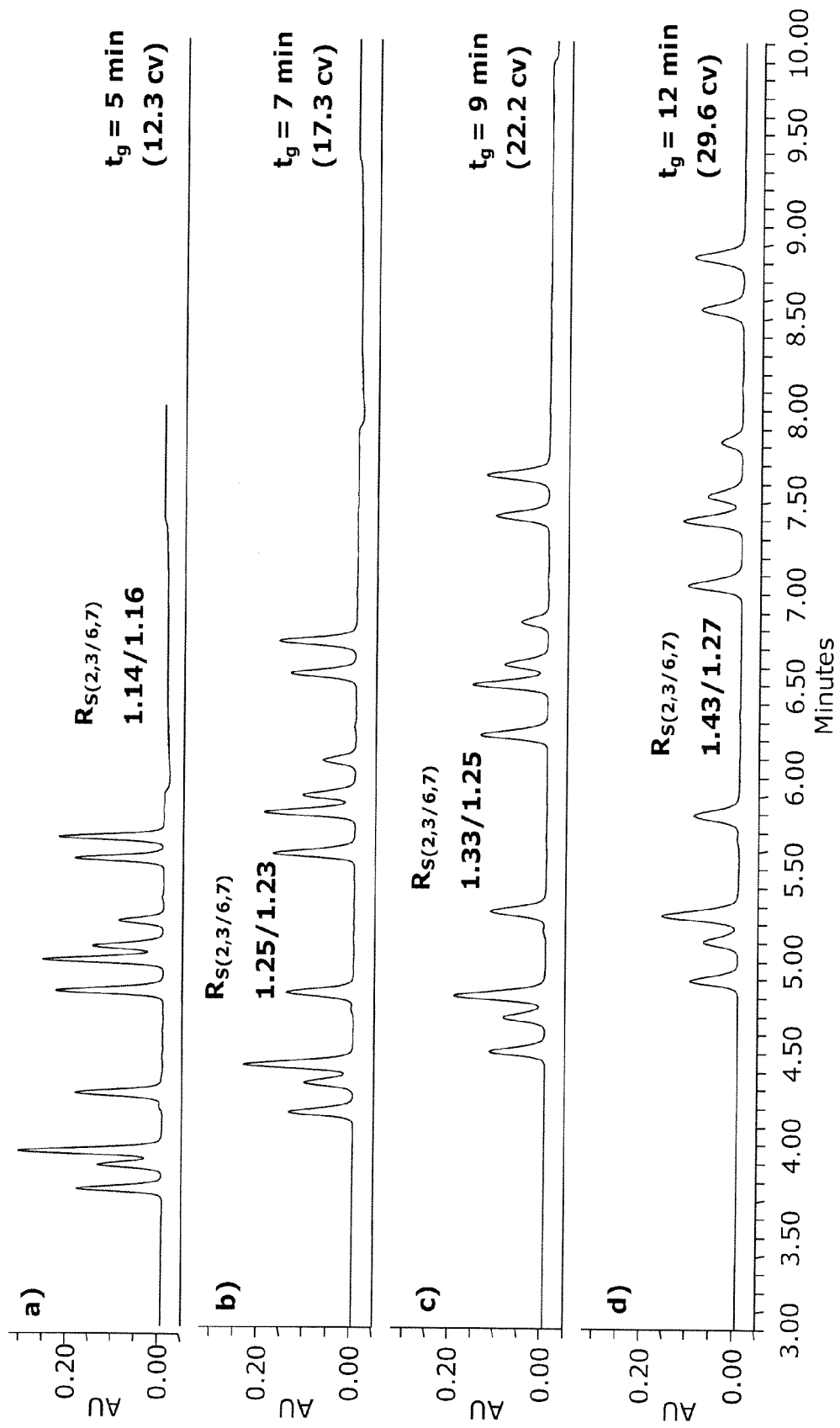
FIG. 15 is an exemplary illustration showing the separation of the estrogen mixture using a chromatography column packed with hybrid particles with a polar surface functionality (i.e., a BEH 2-EP, 1.7 μm, 3.0×100 mm column; Waters Corp., Milford, Mass.) with methanol as the modifier and 0.3% isopropyl amine as the additive, employing a flow gradient from 1.4 to 0.9 mL/min, with 8-33% modifier. For each example, the gradient slope was adjusted by changing the gradient time ($t_g$) as follows: 5 minutes (a), 7 minutes (b), 9 minutes (c), and 12 minutes (d). Each chromatogram was collected at 30° C. with an ABPR setting of 4100 psi. The gradient volumes were 12.3, 17.3, 22.2, and 29.6 column volumes, respectively. The peak identities in this figure correspond to those shown in FIG. 9, panel (a).

The slope of the gradient can also have significant impact on the separation. The slope can be explored by altering either the beginning and ending modifier concentrations or by increasing or decreasing the gradient time ($t_g$). FIG. 15 demonstrates the effect of altering the starting and ending modifier concentration for the gradient, while holding the gradient time constant. The optimum resolution for the critical pairs is obtained with the shallowest gradient evaluated (8-33% modifier). Using these starting and ending modifier concentration values for the gradient, further evaluation of the gradient slope was explored by altering the length of the gradient ($t_g$). FIG. 15 shows the effect of increasing and decreasing the slope of the gradient by altering the length of the gradient, or the number of column volumes used during the gradient separation. The greatest resolution of the critical pairs is again obtained with the shallowest gradient (8-33% modifier in 12 minutes or ~2% per minute), as shown in FIG. 15.

(VII) Additional Optimization

Figure 16:
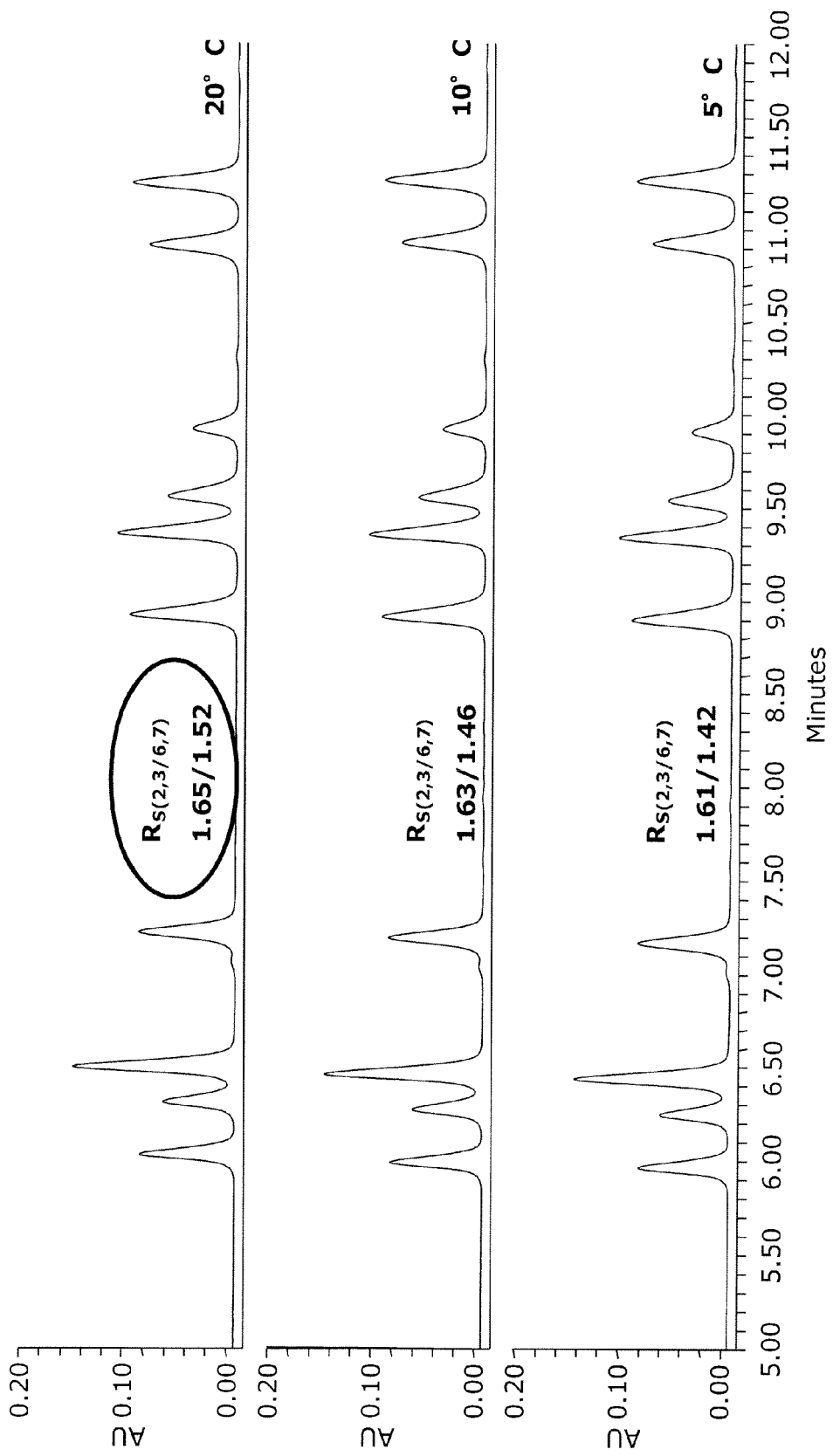
FIG. 16 is an exemplary illustration showing the separation of the estrogen mixture using a chromatography column packed with hybrid particles with a polar surface functionality (i.e., a BEH 2-EP, 1.7 μm, 3.0×100 mm column; Waters Corp., Milford, Mass.) with methanol as the modifier and 0.3% isopropyl amine as the additive, employing a 12 minute gradient from 8-27% modifier, a flow gradient from 1.4 to 0.9 mL/min. The temperatures were 20° C. (top), 10° C. (middle), and 5° C. (bottom). Each chromatogram was collected with an ABPR setting of 4100 psi. The separation at 20° C. met the resolution criteria required for the current separation. The peak identities in this figure correspond to those shown in FIG. 9, panel (a).

The goal of this method development was to obtain resolution values >1.5 for each of the analytes. While the best separation in the previous example approaches this criteria, additional optimization was still required. During the temperature evaluations, the optimum separation was achieved at 30° C., but lower temperatures were not explored. For additional optimization, lower temperatures were evaluated, with an additional adjustment to decrease the slope of the gradient. Temperatures of 20, 10, and 5° C. were evaluated with a 12-minute gradient from 8-27% modifier (~1.6% per minute). The results of these evaluations are shown in FIG. 16. FIG. 16 shows that the goals for this separation, Rs>1.5 for all analytes, can be achieved at 20° C., using the shallower gradient of 8-27% modifier in 12 minutes.

(VIII) Alternatives Separations

Figure 17:
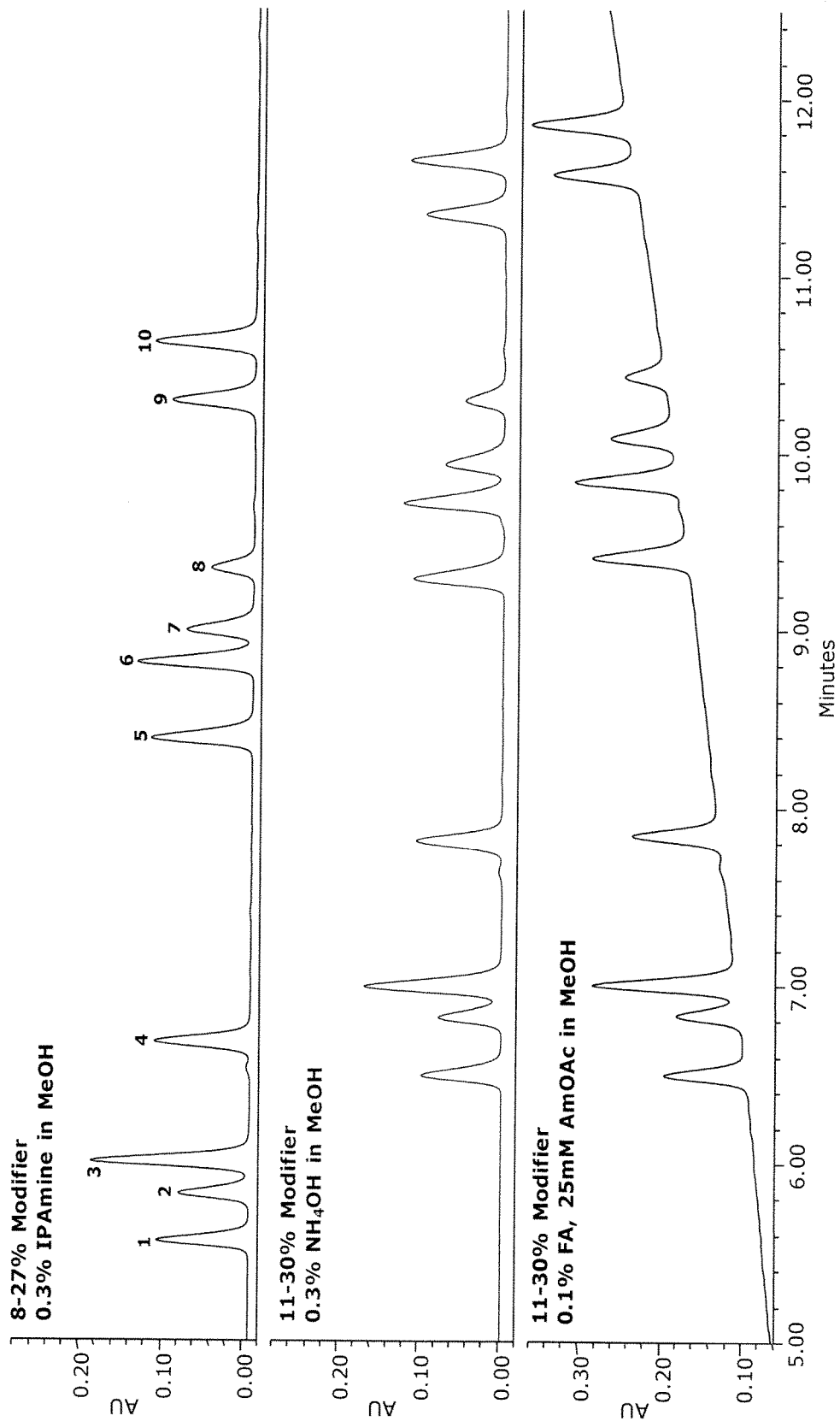
FIG. 17 is an exemplary illustration showing the separation of the sulfated estrogen mixture using a chromatography column packed with hybrid particles with a polar surface functionality (i.e., a BEH 2-EP, 1.7 μm, 3.0×100 mm column; Waters Corp., Milford, Mass.) with methanol as the modifier and with various additives as follow: 0.3% isopropyl amine (top), 0.3% ammonium hydroxide (middle), and 0.1% formic acid with 25 mM ammonium acetate (bottom). For each separation 12 minute gradients with equal slopes were used: 8-27% (top) and 11-30% (middle and bottom). Each separation also utilized a flow gradient from 1.4 to 0.9 mL/min. The data was collected at a temperature of 20° C. with an ABPR setting of 4100 psi. The peak identities in this figure correspond to those shown in FIG. 9, panel (a).

During the initial evaluation of additives, based on the goals set forth for this method, isopropyl amine was chosen for additional optimization. If the method were to incorporate mass spectrometry, optimization may have been focused on another additive, either the ammonium hydroxide or the formic acid/ammonium formate additive because of their increased compatibility with the mass spectrometry system. Purely as an exploratory exercise, these two additives were re-evaluated with the current optimized method. Based on the increased retention observed during the initial additive evaluations (shown in FIG. 9), the modifier concentrations were increased slightly (3%), while keeping all other parameters constant, including the gradient slope. FIG. 17 shows the optimum separation achieved with the isopropyl amine additive, using the optimized gradient from 8-27% modifier, along with the separations of the two alternative modifiers, utilizing a gradient from 11-30% modifier. This exercise demonstrates the versatility of Convergence Chromatography, with the flexibility to alter conditions to accommodate different detection methods.

CONCLUSIONS

The method development for sulfated estrogens involved several critical parameters for an optimal separation, including column chemistry, choice of modifier, additive, pressure, temperature, flow rate, and gradient slope. Although the choice of additive had minimal impact on overall selectivity, the presence of the additive is critical for elution of these charged analytes, and can impact the peak shape and resolution for the analytes. The importance of pressure cannot be understated, and the application of reverse flow-gradients to maintain the highest possible flow rates and greatest efficiencies can be extremely beneficial, while staying within the pressure limitations of the system.

The application of the present technology to the separation of sulfated estrogens represents a dramatic improvement over conventional gas chromatographic methods, with greater than 90% reduction in overall analysis time for the synthetic mixture of 10 sulfated estrogens. This is mostly due to the improvement in workflow provided by the elimination of sample desulfation and derivatization requirements prior to analysis. The reduction in the complexity and time requirements for the sample preparation yields increased laboratory efficiency with less opportunity for compounded errors. As demonstrated in this study, the ability for the system and method of the subject technology to separate compounds with very similar structures makes it well suited for the analysis of steroid and steroid-related compounds.

Example 4

Analysis of Endogenous Steroids

Figure 18:
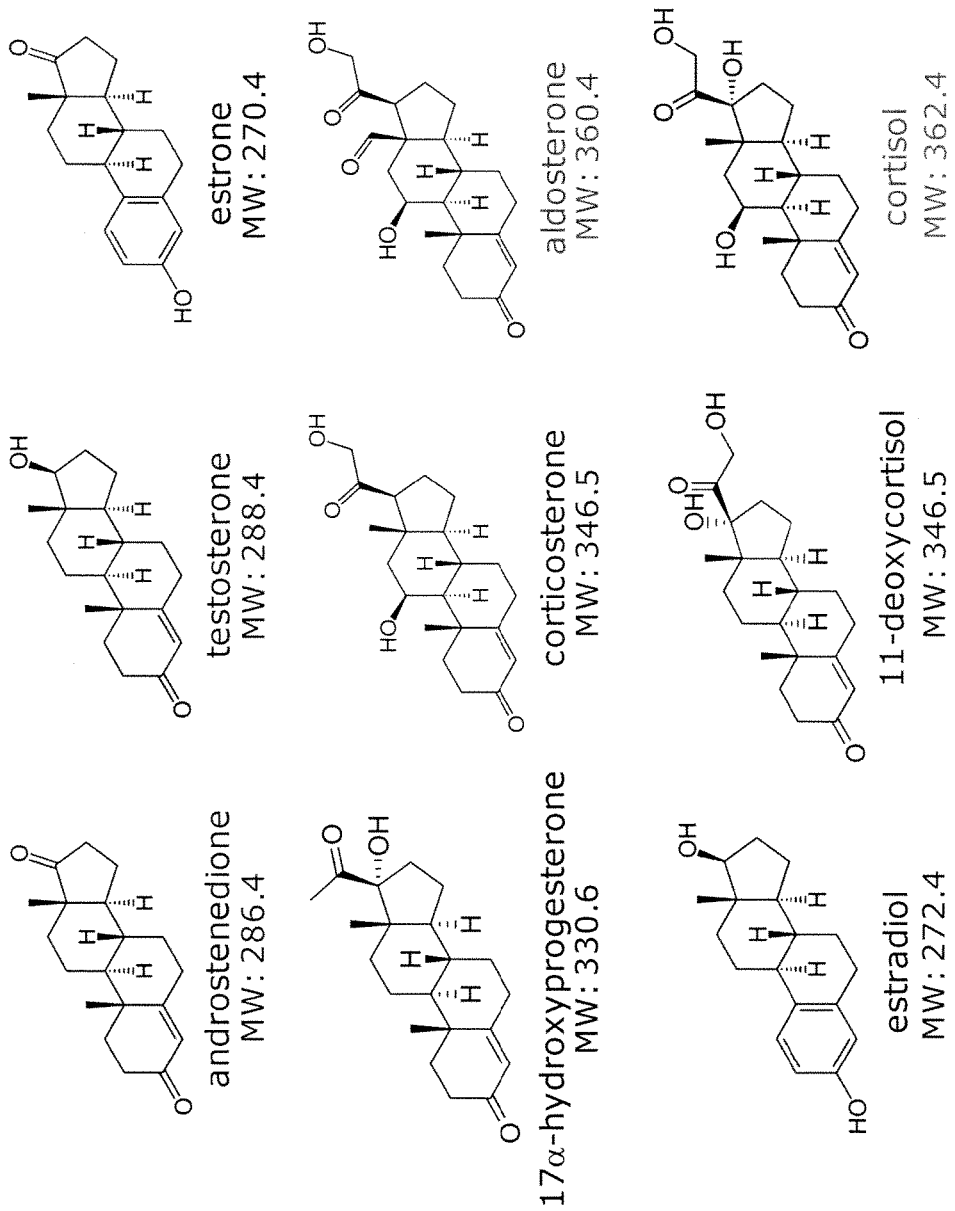
FIG. 18 shows the chemical structures of the steroids studied in Example 4.

This study focuses on the application of the method and system of the subject technology for the rapid chromatographic analysis of endogenous steroids (structures shown in FIG. 18. As will be shown and discussed below, the method and system of the subject technology result in the analysis of steroids in approximately 2 minutes. After initial method development using UV detection, the system was coupled to a tandem quadrupole mass spectrometer for analysis of steroid-spiked plasma samples. In addition to the significant reduction in analysis time relative to other techniques, the method and system of the subject technology minimizes the consumption of mobile phase solvents (e.g. methanol), thereby generating less waste for disposal and significantly reducing the cost of analysis per sample.

Experimental:

Sample Preparation

Column Screening (UV detection): A mixture of the 9 steroid standards (depicted in FIG. 18) was prepared at 0.2 mg/mL each, using a diluent of 88:12 methanol/ethanol.

Mass Spec Evaluations: Often times matrix interferences can limit the applicability of a technique. For this reason, standards were evaluated in a human plasma matrix. However, to insure these evaluations were indicative of technique sensitivity, and not affected by recovery issues during sample preparation, the plasma samples were post-spiked after a 3:1 acetonitrile protein crash of the plasma. After centrifugation, the supernatant was collected and spiked with a mixture of the 9 steroid standards. Spiking of steroids to various levels was achieved by serial dilution of the sample with additional crashed plasma.

Conditions:

Column Conditions: Chromatography Columns: (1) 3.0 mm (ID)×50 mm (length) column packed with hybrid particles with free surface silanol groups and no additional surface modifications (i.e., BEH column) with a mean particle diameter of 1.7 µm; (2) 3.0×50 mm column packed with hybrid particles with polar surface modifications and not endcapped (i.e., BEH 2-thylpyridine) with a mean particle diameter of 1.7 µm; (3) 3.0×50 mm column packed with hybrid particles coated with low-level surface charges, functionalized with polar surface modifications and not endcapped (i.e., CSH Fluoro-Phenyl) with a mean particle diameter of 1.7 µm; and (4) 3.0×50 mm column packed with silica particles surface modified with $C_{18}$ groups and not endcapped (i.e., HSS C18 SB) with a mean particle diameter of 1.8 µm.

System Conditions: $CO_2$-based column chromatography system (e.g., ACQUITY $UPC^2$ with PDA detector from Waters, Milford, Mass.); Mobile Phase: $CO_2$ (tank, medical grade); Modifier B: Methanol (Fisher Optima® grade); Column Temp.: 40° C.; ABPR: 1800 psi; Gradient: 2-17% Modifier B in 2 minutes, re-equilibration at 2% Modifier B for 1 minute; Flow Rate: 3.65 mL/min; UV Detection: 220 nm (Compensated 380-480 nm) [40 pts/sec]; Injection Volume: 1 µL; Needle Wash: 50:50 methanol/2-propanol; Seal Wash: Methanol; Data System: Empower® 3 Software.

Make-up Flow Pump: Solvent: Methanol with 2.5% water and 0.1% ammonium hydroxide; Flow Rate: 0.4 mL/min Mass Spec: System: Xevo TQ-MS; Capillary Voltage: 1 kV; Desolv. Temp.: 500° C.; Desolv. Gas Flow: 750 L/hr; Data System: Mass Lynx® 4.1.

Results and Discussion:

A generic 2-minute screening gradient was used to evaluate the separation of the 9 steroid mixture on four different stationary phases to determine which would provide the best separation. The chromatograms in FIG. 19 demonstrate the selectivity differences of the stationary phases, as well as the inherent speed of this chromatographic technique. Based on these results, the BEH stationary phase was chosen for additional application development with mass spectrometric detection.

Individual mass spec (MRM) transitions were optimized by direct infusion of standards into the Xevo TQ MS using the on-board fluidics, without the connectivity of the $CO_2$ based system of the subject technology (Table 3). After optimization of transitions, the Mass Spec system was coupled to the $CO_2$ based system using a Mass Spec splitter, incorporating the addition of a make-up flow pump, to facilitate sample flow into the MS and subsequent ionization (FIG. 3).

TABLE 3

Multiple Reaction Monitoring (MRM) transitions used for the analysis of 9 structurally related steroids. Mass Spec conditions for the MRM transitions were optimized using IntelliStart ™ in infusion mode only (without the $CO_2$ based system). MRM transitions in bold are transitions chosen for monitoring.

| Compound | Precursor | Product | Collision Energy | Dwell | Cone Voltage | Mode |
|---|---|---|---|---|---|---|
| estrone | 271.05 | 153.1 | 30 | 0.005 | 25 | ESI+ |
|  |  | 253.2 | 15 |  |  |  |
| andro- stenecdione | 287.05 | 97.15 | 21 | 0.005 | 25 | ESI+ |
|  |  | 109.2 | 26 |  |  |  |
| testosterone | 289.10 | 97.15 | 21 | 0.005 | 25 | ESI+ |
|  |  | 109.15 | 26 |  |  |  |
| 17α-hydroxy progesterone | 331.10 | 97.15 | 21 | 0.005 | 25 | ESI+ |
|  |  | 109.1 | 26 |  |  |  |
|  |  | 313.3 | 16 |  |  |  |
| 11- deoxy- cortisol | 347.05 | 97.11 | 24 | 0.005 | 26 | ESI+ |
|  |  | 109.14 | 26 |  |  |  |
| cortico- sterone | 347.05 | 105.1 | 42 | 0.005 | 24 | ESI+ |
|  |  | 121.1 | 28 |  |  |  |
| aldosterone | 361.05 | 97.15 | 35 | 0.005 | 25 | ESI+ |
|  |  | 315.2 | 20 |  |  |  |
|  |  | 343.2 | 16 |  |  |  |
| cortisol | 363.05 | 121.2 | 25 | 0.005 | 25 | ESI+ |
|  |  | 309.2 | 20 |  |  |  |
|  |  | 327.2 | 15 |  |  |  |
| estradiol | 271.00 | 145.1 | 38 | 0.005 | 55 | ESI+ |
|  |  | 183.1 | 38 |  |  |  |

Optimization of Make-Up Flow

The make-up flow introduced through the Mass Spec Splitter has a dual purpose. It facilitates the post-mixer transfer of the sample, through the tubing as the $CO_2$ in the mobile phase starts to decompress as it reaches the mass spec. This is especially important at low concentrations of the organic modifier in the mobile phase, as is seen in the early stages of the current gradient profile. In addition, the use of additives in the make-up flow (e.g. water, ammonium hydroxide [NH4OH], or formic acid [FA]) can assist in ionization of the analytes within the mass spec source, improving sensitivity. To optimize the make-up flow and additional mass spec conditions, a plasma sample spiked with the 9 steroids (at 50 ng/mL) was used to evaluate various conditions: additive used in make-up flow solvent, capillary voltage, desolvation temperature and gas flow (data not shown).

Figure 20:
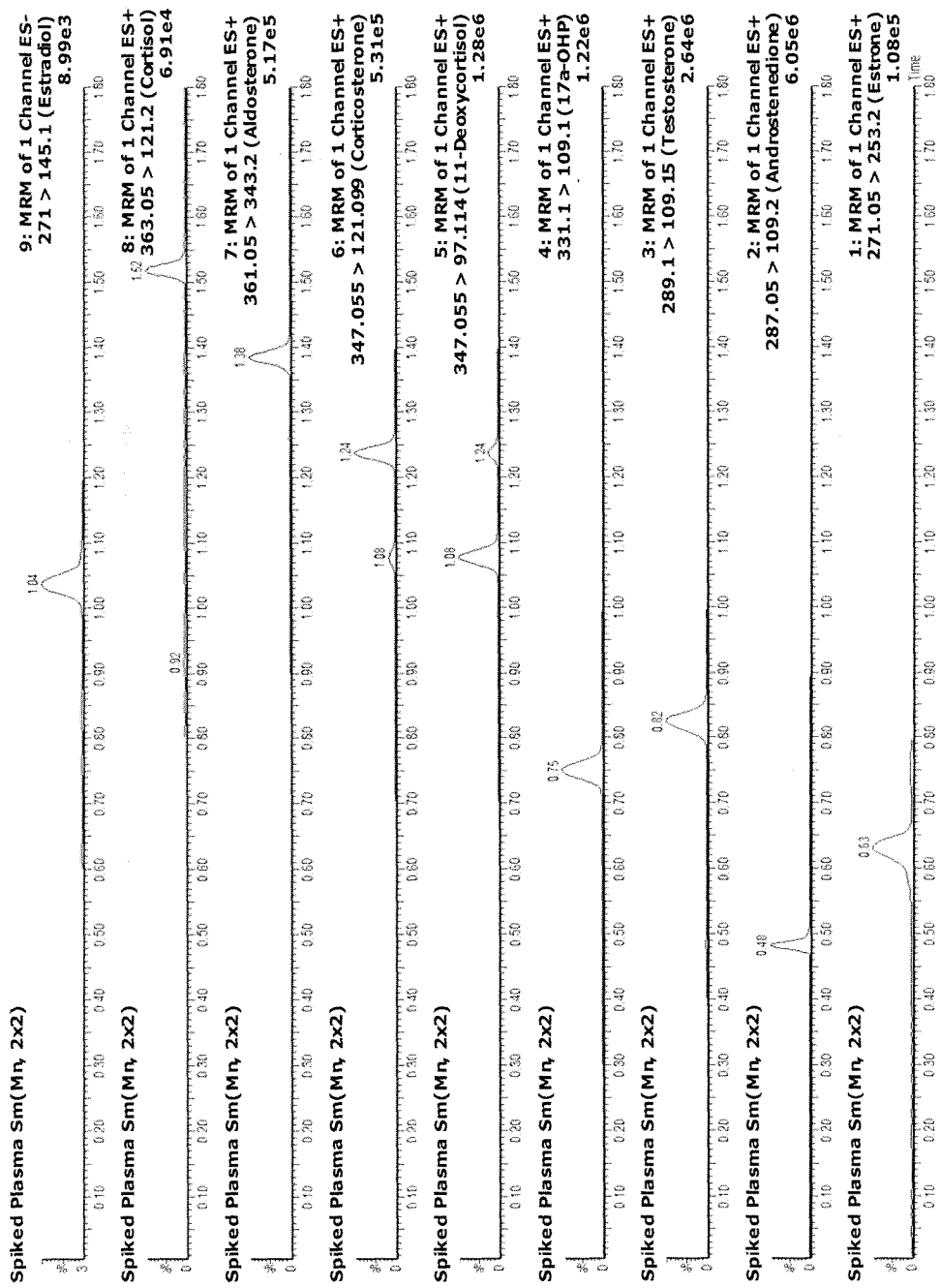
FIG. 20 is an exemplary illustration showing the Total Ion Chromatograms (TIC) of the 9 steroids studied in Example 4. Standards were post spiked at a concentration of 50 ng/mL into a 3:1 acetonitrile protein crash of human plasma.

The optimization tests showed that 8 of the 9 steroids yielded higher MS signals (better ionization) when using ammonium hydroxide as an additive in the make-up flow. In addition, most of the steroid signals were ambivalent to capillary voltages between 0.8 and 3.0 kV (FIG. 4—middle). However, at voltages higher than 1.0 kV, the signal for cortisol diminished dramatically. Based on these evaluations, the optimum conditions were determined, with the best overall signal obtained for all steroids using a make-up solvent composed of methanol with 2.5% water and 0.1% ammonium hydroxide, and a flow rate of 0.4 mL/min. The optimum results were obtained by mass spec when using a capillary voltage of 1.0 kV, with a desolvation temperature of 500° C. and a gas flow of 750 L/hr (FIG. 4—bottom). The resulting chromatography is shown in FIG. 20 for the 9 steroids post-spiked into the human plasma after protein crash.

Reproducibility

As with any method development, the accuracy and reproducibility of the method is critical for success. To evaluate reproducibility of the method, the peak areas for the individual steroids were monitored over the course of 100 injections (using 1 μL injection volumes of 50 ng/mL steroid spiked in plasma). The RSD values for the peak areas ranged from 5.6 to about 13.7% (data not shown).

To evaluate the linearity of response, calibration curves were generated using 5 μL injections of the spiked steroid plasma samples (after 3:1 acetonitrile protein crash). Concentrations of the steroids ranged from 0.98 to 500 ng/mL. All of the calibration curves showed a correlation coefficient of greater than 0.99 with $R^2$ of greater than 0.99 (data not shown).

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A chromatography method for detecting one or more steroids or steroid derivatives in a sample comprising the steps of:
    providing a sample comprising one or more steroids or steroid derivatives for analysis; wherein the sample is prepared with, extracted or dissolved in a diluent comprising at least about 60% organic solvent, with the proviso that the sample is analyzed without a solvent exchange step;
    applying the sample to a chromatography column with a solid stationary phase comprising inorganic or hybrid particles having a mean particle size of about 0.5 to about 3.5 microns; wherein said hybrid particles comprise an inorganic portion and an organic portion wherein the organic portion of the hybrid particles comprises substituted or unsubstituted C1-C18 alkane, alkylene, alkenylene, alkynylene or arylene moiety bonded to one or more atoms of the inorganic portion; and wherein said inorganic or hybrid particles have a polar or polar/non-polar surface functionality and retain said one or more steroids or steroid derivatives;
    eluting the one or more steroids or steroid derivatives from the chromatography column by a mobile phase comprising a mixture of $CO_2$, and a modifier to form one or more eluted steroids or steroid derivatives; and
    detecting said one or more eluted steroids or steroid derivatives.

2. The method of claim 1, wherein the sample comprises a biological sample or a non-biological sample or a mixture thereof.

3. The method of claim 1, wherein the particles have a mean particle size of about 0.5 to about 2 microns.

4. The method of claim 1, wherein the particles have a mean pore volume in the range of about 0.1 to about 2.5 $cm^3/g$.

5. The method of claim 1, wherein the particles have a mean pore diameter in the range of about 100 to about 1000 Angstroms.

6. The method of claim 1, wherein the inorganic particles comprise silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof.

7. The method of claim 1, wherein the inorganic portion of the hybrid particles comprises comprise silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof.

8. The method of claim 1, wherein the organic portion of the hybrid particles comprises substituted or unsubstituted C1-C18 alkylene, alkenylene, alkynylene or arylene moiety bridging two or more atoms of the inorganic portion.

9. The method of claim 1, wherein the particles comprise free surface hydroxyl groups, free surface silanol groups or surface modifications with embedded polar functional groups.

10. The method of claim 1, wherein the particles comprise free surface hydroxyl groups or free surface silanol groups and surface modifications with non-polar functional groups.

11. The method of claim 1, wherein the chromatography column is kept in temperature range of about 5° C. to about 85° C.

12. The method of claim 1, wherein the modifier is mixed with the $CO_2$ under a constant or gradient condition or both over an elution period or a fraction thereof.

13. The method of claim 1, wherein the modifier is a polar water-miscible organic solvent comprising at least one of methanol, ethanol, isopropanol, acetonitrile, acetone, tetrahydrofuran or water.

14. The method of claim 12, wherein the gradient condition comprises increasing or decreasing flow volume of the modifier over the elution period or a fraction thereof.

15. The method of claim 14, wherein the elution period is about 2 min.

16. The method of claim 14, wherein the gradient condition comprises increasing the flow volume of the modifier from about 0% to about 40% (v/v $CO_2$) or any intervals therebetween.

17. The method of claim 14, wherein the gradient condition comprises increasing the flow volume of the modifier from about 1% to about 17% (v/v $CO_2$).

18. The method of claim 1, wherein the $CO_2$ is liquid $CO_2$ in subcritical or supercritical state or both.

19. The method of claim 1, wherein the detection comprises determining the level or the presence or absence of the one or more steroids or steroid derivatives.

20. The method of claim 1, wherein the detection is by way of a UV detector; a mass spectrometer; Evaporative Light Scattering (ELS) detector or a photodiode array detector (PDA).

21. The method of claim 1, wherein the sample is not subject to a derivatization step.

22. The method of claim 1, wherein the chromatography column has a length of about 50 to 150 mm and an internal diameter about 2 to 4 mm.

23. The method of claim 1, wherein the chromatography column is part of a chromatography system comprising a pre-column mobile phase dwell volume of about 75 to about 500 µL; wherein said pre-column mobile phase dwell volume is the volume of the mobile phase present in a fluidic connection between a junction at which the $CO_2$ and the modifier are mixed and the head of the chromatography column.

24. The method of claim 1, wherein the one or more steroids or steroid derivatives are eluted from the chromatography column by the mobile phase with a flow rate of about 1 to 4 mL/min.

25. A chromatography method for detecting one or more steroids or steroid derivatives in a sample comprising the steps of:
providing a sample comprising one or more steroids or steroid derivatives for analysis; wherein the sample is prepared with, extracted or dissolved in a diluent comprising at least about 60% organic solvent, with the proviso that the sample is analyzed without a solvent exchange step;
applying the sample to a chromatography column with a solid stationary phase comprising inorganic or hybrid particles having a mean particle size of about 0.5 to about 3.5 microns; wherein said particles retain said one or more steroids or steroid derivatives and wherein said particles comprise 1) free surface hydroxyl groups, free surface silanol groups or surface modifications with embedded polar functional groups; or 2) free surface hydroxyl groups or free surface silanol groups and surface modifications with non-polar functional groups;
eluting the one or more steroids or steroid derivatives from the chromatography column by a mobile phase comprising a mixture of $CO_2$, and a modifier to form one or more eluted steroids or steroid derivatives; and
detecting said one or more eluted steroids or steroid derivatives.

26. A chromatography method for detecting one or more steroids or steroid derivatives in a sample comprising the steps of:
providing a sample comprising one or more steroids or steroid derivatives for analysis; wherein the sample is prepared with, extracted or dissolved in a diluent comprising at least about 60% organic solvent, with the proviso that the sample is analyzed without a solvent exchange step;
applying the sample to a chromatography column with a solid stationary phase comprising inorganic or hybrid particles having a mean particle size of about 0.5 to about 3.5 microns; wherein said particles have a polar or polar/non-polar surface functionality and retain said one or more steroids or steroid derivatives;
eluting the one or more steroids or steroid derivatives from the chromatography column by a mobile phase comprising a mixture of $CO_2$, and a modifier to form one or more eluted steroids or steroid derivatives, wherein the modifier is mixed with the $CO_2$ under a gradient condition comprising increasing the flow volume of the modifier from about 1% to about 17% (v/v $CO_2$) over an elution period or a fraction thereof; and
detecting said one or more eluted steroids or steroid derivatives.

* * * * *